United States Patent [19]
Brion et al.

[11] Patent Number: 5,959,146
[45] Date of Patent: Sep. 28, 1999

[54] TRICYCLIC COMPOUNDS

[75] Inventors: Francis Brion, Gagny; Bernadette Chappert, Paris; Christian Diolez, Palaiseau; Christian Marie, Noisy le Sec; Alain Mazurie, Vaujours; Michel Middendorp, Faremoutiers; Didier Pronine, Rosny Sous Bois; Edmond Toromanoff, Paris, all of France

[73] Assignee: Hoechst Marion Roussel, France

[21] Appl. No.: 08/764,863

[22] Filed: Dec. 13, 1996

Related U.S. Application Data

[62] Division of application No. 08/609,679, Mar. 1, 1996, Pat. No. 5,705,704.

[30] Foreign Application Priority Data

Mar. 3, 1995 [FR] France .................................. 95 02480

[51] Int. Cl.⁶ ................................................ C07C 233/05
[52] U.S. Cl. ........................... 564/200; 564/199; 564/221; 564/222
[58] Field of Search ..................... 564/221, 222, 564/199, 200

[56] References Cited

PUBLICATIONS

J. of Chemical Soc., Perkin Transactions, 2, Letchworth GB, pp. 2201–2204, 1992.
J. of Organic Chemistry, vol. 56, No. 1, Easton US, pp. 428–432, 1991.
Heterocycles, vol. 36, No. 11, pp. 2531–2540, 1993.
Chemical Absracts, vol. 115, No. 3, pp. 441, T. Hiroshi et al. 1991.
Heterocycles, vol. 25, No. 1, Walterova et al, pp. 89–96, 1987.
Bul. De La Soc. Chim. De France, No. 6, Paris FR, Deloraff et al, pp. 1621–1627, 1965.
Chemical Abstracts, vol. 47, No. 2, Columbus, 1953.
Santavy, vol. 46, pp. 280–289, 1952.
Chemical Abstracts, vol. 88, No. 17, Ohio, Kieslev et al, p. 572, 1978.
Hev. Chim. Acta., vol. 33, Basal CH, Santavy et al, pp. 1606–1627, 1950.
J. Org. Chem, vol. 51, No. 13, Easto US, pp. 2515–2521, Dumount et al. 1986.
J. Chem. Soc, Chem. Communi., Letchworth GB, pp. 390–392, 1967.
Martel et al, C.R.Acad. Sc. Paris, t.258, pp. 243–245, Group 8, 1964.
Martel et al, J. Org. Chem., vol. 30, pp. 1752–1759, 1965.

*Primary Examiner*—Shailendra Kumar
*Attorney, Agent, or Firm*—Bierman, Muserlian and Lucas

[57] ABSTRACT

Novel tricyclic compounds of formula I as defined in the specification, a process for their preparation and their use for the preparation of optically active or racemic colchicine and thiocolchicine derivatives.

17 Claims, No Drawings

TRICYCLIC COMPOUNDS

PRIOR APPLICATIONS

This application is a division of U.S. patent application Ser. No. 609,679 filed Mar. 1, 1996, now U.S. Pat. No. 5,705,704.

OBJECTS OF THE INVENTION

It is an object of the invention to provide the novel compounds of formula I and a process of preparing the same.

It is another object othe invention to provide a novel process for the preparation of the compounds of formula II.

These and other objects and advantages of the invention will become obvious from the following detailed description.

THE INVENTION

The novel tricyclic compounds of the invention have the formula

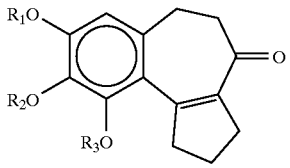

(I)

wherein a) $R_1$ and $R_2$ are alkyl of 1 to 6 carbon atoms and $R_3$ is hydrogen or A—$SO_2$— or b) $R_2$ and $R_3$ are hydrogen and $R_1$ is A—$SO_2$— or c) $R_1$, $R_2$ and $R_3$ are all hydrogen or all alkyl of 1 to 6 carbon atoms or d) $R_1$ is A—$SO_2$— or hydrogen and $R_2$ and $R_3$ together with the oxygens to which they are attached form —O—X—O—, X is selected from the group consisting of —B(OR$_4$)—, —C(O)— and —CR$_5$R$_6$—, $R_4$ is hydrogen or alkyl of 1 to 6 carbon atoms, $R_5$ and $R_6$ are individually selected from the group consisting of hydrogen, alkyl of 1 to 6 carbon atoms and phenyl optionally substituted with 1 to 3 members of the group consisting of —OH and alkyl and alkoxy of 1 to 6 carbon atoms or $R_5$ and $R_6$ together with the carbon atoms to which they are attached form a carbocyclic of 5 to 6 carbon atoms or e) $R_3$ is A—$SO_2$— and $R_1$ and $R_2$ together with the oxygens to which they are attached form —O—X—O— or f) $R_1$ is hydrogen and $R_2$ and $R_3$ are both alkyl of 1 to 6 carbon atoms or together with the oxygens to which they are attached form —O—X—O— and A is selected from the group consisting of alkyl of 1 to 6 carbon atoms, phenyl optionally substituted with 1 to 3 alkyls of 1 to 6 carbon atoms and naphthyl optionally substituted with 1 to 5 alkyls of 1 to 6 carbon atoms.

Examples of alkyl of 1 to 6 carbon atoms are methyl, ethyl, propyl, isopropyl, butyl, tert.-butyl, isobutyl, pentyl and hexyl. If $R_1$, $R_2$, $R_3$, $R_5$ and $R_6$ are alkyl, they may be the same or different. Examples of alkoxy of 1 to 6 carbon atoms are methoxy, ethoxy, isopropoxy, butoxy, etc.

Among the preferred compounds of formula I are those wherein $R_1$, $R_2$ and $R_3$ are all hydrogen or all alkyl, preferably methyl, those wherein $R_1$ is A—$SO_2$—, preferably tosyl and $R_2$ and $R_3$ are both hydrogen or both alkyl, preferably methyl, and those wherein $R_1$ is hydrogen and $R_2$ and $R_3$ are both methyl.

The process for the preparation of a compound of formula I comprises i) reacting a compound of the formula

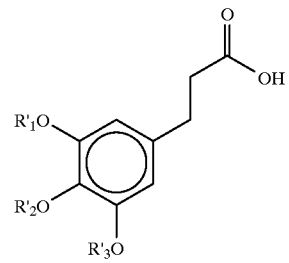

a wherein $R'_1$, $R'_2$ and $R'_3$ respectively have the meaning as $R_1$, $R_2$ and $R_3$ as defined, with the exception of hydrogen and for $R'_3$ —A— $SO_2$—, with a halogenation agent to obtain the corresponding acyl halide, ii) reacting the latter with a reagent of the formula

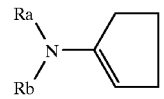

b wherein Ra and Rb individually are alkyl of 1 to 6 carbon atoms, or Ra and Rb together with the nitrogen atom to which they are attached form a heterocycle of 5 or 6 members optionally containing another heteroatom selected from 0 and N to obtain a compound of the formula

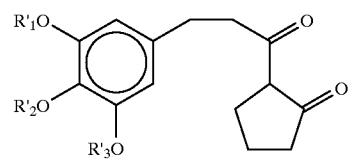

c iii) reacting the latter with a halogenation agent to obtain a compound of the formula

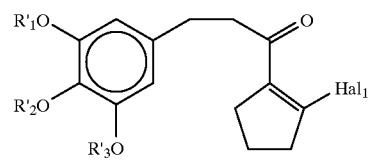

d wherein Hal$_1$ is halogen, iv) reacting the latter with a Lewis acid to obtain a compound of the formula:

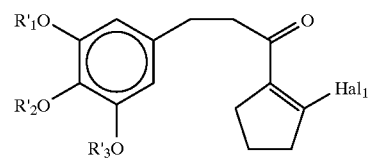

e corresponding to the compounds of formula I (a) as defined above in which $R_3$ is A—$SO_2$—, to the compounds of formula I (c) as defined above in which all three of $R_1$, $R_2$ and $R_3$ are alkyl and to the compounds of formula I (e), as defined above, optionally reacting the compound of formula (e), v)—either if $R'_1$ is A—SO$_2$— and $R'_2$ and $R'_3$ do not together represent —X—, with a hydrolysis agent to obtain a compound of formula

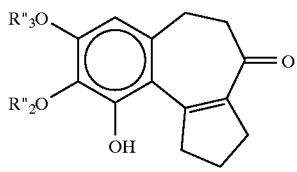

f in which $R''_2$ and $R''_3$ both are alkyl corresponding to the compounds of formula I (a) as defined above in which $R_3$ is hydrogen, optionally reacting the latter with an alkylation agent to obtain a compound of the formula

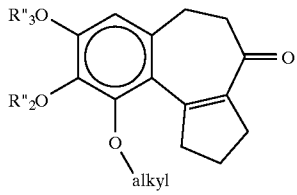

g corresponding to the compounds of formula I (c) as defined above, in which $R_1$, $R_2$ and $R_3$ are alkyl, optionally subjecting the latter to a hydrolysis of all alkoxys to obtain a compound of the formula

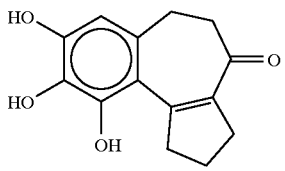

h corresponding to the compound of formula I (c) as defined above, in which $R_1$, $R_2$ and $R_3$ are hydrogen, viii) or subjecting a compound of formula (e) in which all three of $R'_1$, $R'_2$ and $R'_3$ are alkyl, to a hydrolysis of all alkoxys to obtain the compound of formula (h) defined above, ix) optionally reacting the latter with a protection reagent of diols chosen from compounds of the formulae:

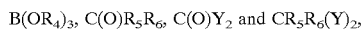

B(OR$_4$)$_3$, C(O)R$_5$R$_6$, C(O)Y$_2$ and CR$_5$R$_6$(Y)$_2$, wherein $R_4$, $R_5$ and $R_6$ are as defined above and Y is halogen or Ar—O— in which Ar is phenyl optionally substituted by 1 to 3 substituents selected from the group consisting of alkyl, alkoxy, hydroxy, amino, alkylamino, dialkylamino and nitro; or with a reagent of the formula CH$_2$(Y)$_2$, Y being defined as above, in the presence of a reagent of the formula P(Hal)$_5$, in which Hal is halogen, followed by a hydrolysis to obtain a compound of the formula

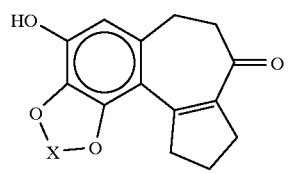

i corresponding to the compounds of formula I (d) as defined above in which $R_1$ is hydrogen, which is treated with an agent of the formula A—SO$_2$Y, in which A is defined as in claim 1 and Y is defined as above to obtain a compound of the formula

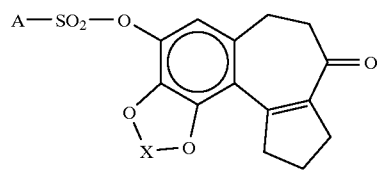

j corresponding to the compounds of formula I (d) as defined above in which $R_1$ is A—SO$_2$—, x) optionally reacting the latter with a deprotection reagent of the diol to obtain a compound of the formula

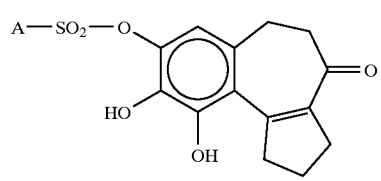

k corresponding to the compounds of formula I as defined above in which $R_2$ and $R_3$ are hydrogen, optionally reacting the latter with an alkylation agent to obtain a compound of the formula

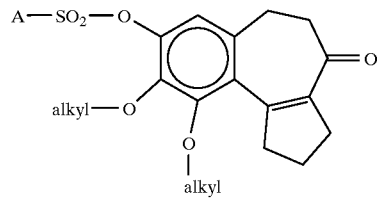

l corresponding to the compounds of formula I (b) as defined above xii) optionally reacting a compound of formula (j) or (l) with a hydrolysis agent of A—SO$_2$—O— to obtain a compound of the formula

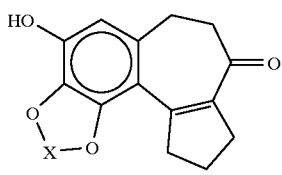

or

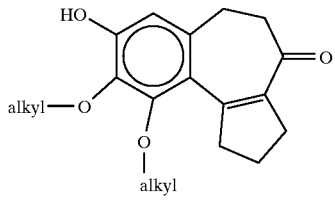

respectively, corresponding to the compounds of formula I (f) as defined above.

Examples of the halogenation agent reacted with the compound of formula a are thionyl chloride, oxalyl chloride and other agents forming an acid halide. The reagent of formula b may be prepared from cyclopentanone and a secondary amine, for example diethylamine, piperidine, piperazine or, preferably, morpholine. The operation is carried out in the presence of a strong acid catalyst such as p-toluene sulfonic acid.

The action of the enamine of formula b on the acid halide is preferably carried out in the presence of a tertiary amine such as triethylamine or pyridine. The halogenation agent which is reacted with the compound of formula c can be, for example, thionyl chloride, phosgene, phosphorus oxychloride or, preferably, oxalyl chloride. The Lewis acid used for the cyclization of the compound of formula d is for example aluminium chloride, titanium tetrachloride, or preferably ferric chloride, or tin tetrachloride. The reaction, as with those which precede, can be carried out in a halogenated solvent such as methylene chloride, chloroform or dichloroethane.

The hydrolysis leading to the compound of formula f, i or l' can be carried out by the action of sodium hydroxide, potassium hydroxide or sodium or potassium carbonate in the presence of an aqueous alkanol. The hydrolysis leading to the compound of formula h can be carried out with a dealkylation agent such as boron tribromide, aluminium chloride, hydrochloric acid, or also a mercaptan such as thiophenol.

The alkylation of the compounds of formulae f and k can be any standard agent known to a man skilled in the art for the alkylation of phenols. There can be mentioned for example an alkyl halide such as methyl or ethyl iodide, an alkyl sulfate such as methyl or ethyl sulfate, or diazomethane. If appropriate, the operation can be carried out in the presence of a base such as a hydroxide or an alkali metal carbonate in an organic solvent, for example a halogenated solvent, and if appropriate, in the presence of a phase transfer agent, for example a quaternary ammonium salt such as tetra-n-butyl ammonium bromide.

The protection reagent of the diols which is reacted with the compound of formula h can be a boron derivative such as boric acid, a trialkyl borate, for example trimethyl or triethyl borate, or also borax. It can also be formalin or a ketone, for example acetone or methylethylketone. The operation is then carried out in an anhydrous strong acid medium. It can also be phosgene, used in an anhydrous alkaline medium, for example in the presence of triethylamine or pyridine. It can also be

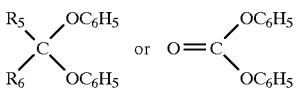

and the operation is then carried out in an anhydrous strong acid medium, for example in the presence of a sulfonic acid. It can also be

and the operation is then carried out in an anhydrous basic medium, for example in the presence of a tertiary amine.

The reagent of formula A—SO$_2$Y which is reacted with the compound of formula i is preferably a sulfonic acid halide ASO$_3$H, in which A is alkyl such as methyl or ethyl, phenyl optionally substituted by one to three alkyls such as tolyl, xylyl or 2,4,6-triisopropylphenyl, or naphthyl.

The deprotection of the diol is carried out either by an acid hydrolysis agent like a strong acid such as hydrochloric acid, sulfuric acid or APTS, or by an oxidizing agent such as hydrogen peroxide in the case of protection by a boron derivative. In the case of protection in the form of an acetonide or carbonate, deprotection is carried out in an aqueous strong acid medium, for example by sulfuric acid, hydrochloric acid or also APTS.

The novel process of the invention for the preparation of a compound of the formula

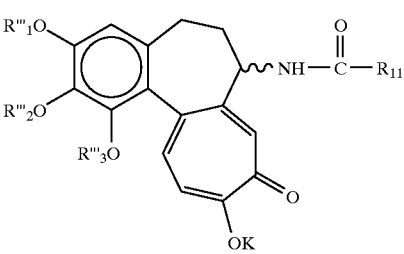

II in which R'''$_1$, R'''$_2$ and R'''$_3$ have the same meanings as R$_1$, R$_2$ and R$_3$ as defined above, with the exception of hydrogen, and, for R$_2$–R$_3$, X other than —CR$_5$R$_6$— and, for R$_1$–R$_2$, X other than —CR$_5$R$_6$—, R$_{11}$ is an alkyl of 1 to 6 carbon atoms, the wavy line indicates that NH—C(O)R$_{11}$ is found in α- or β-position, or that the compound is in the form of a mixture of α- and β-isomers, and K is an alkyl of 1 to 6 carbon atoms, benzyl optionally substituted on the phenyl by 1 to 3 alkyls of 1 to 6 carbon atoms, or —SO$_2$—A', in which A' is chosen independently from the values of A above comprises:

(i) either reacting a compound of formula I wherein R$_2$ or R$_3$ are not hydrogen with an agent of the formula

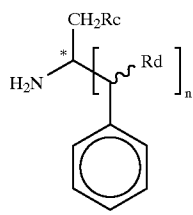   m

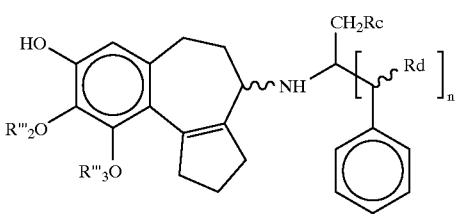   n' in which $R'''_2$, $R'''_3$, $R_c$, $R_d$, n and the wavy lines have the above meaning, subjecting the latter to hydrogenolysis of the alkylamino to obtain a compound of the formula

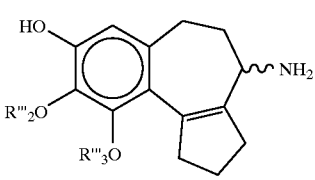   o' in which the wavy line is defined as above, the amino group of being protected with a bivalent protective group to obtain a compound of the formula

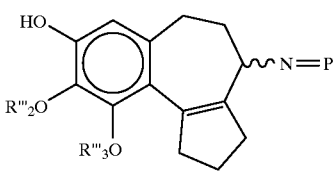   p' in which P and the wavy line have the above meaning, reacting the latter with a protective agent of the hydroxy to obtain a compound of formula (p) as defined previously;

(ii) or reacting a compound of formula I (f) as defined above with an agent of formula m defined above, reacting the imino intermediate obtained with a reducing agent to obtain a compound of formula n' as defined above, and then the synthesis is continued as indicated above;

(iii) or reacting a compound of formula I as defined above with an agent of the formula $R_8O$—$NH_2$, or a salt thereof, in which $R_8$ is hydrogen or alkyl of 1 to 6 carbon atoms to obtain a compound of the formula

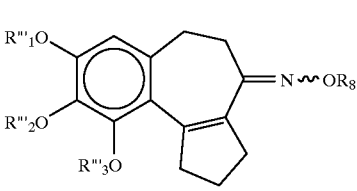   q in which the wavy line indicates that the compound consists of a mixture of syn and anti isomers, (iv) or reacting a compound of formula I as defined above with either a chiral reducing agent, or a non-chiral reducing agent to obtain the corresponding alcohol of the formula in racemic or optically active form, in which Rc and Rd are individually hydrogen or hydroxy and n is 0 or 1; reacting the imino intermediate thus obtained with a reducing agent to obtain a compound of the formula

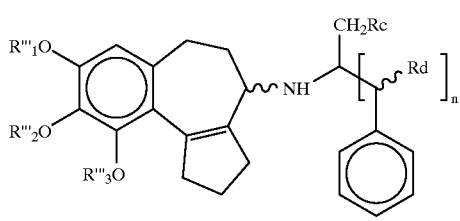   n in which Rc and Rd have the above meanings and the wavy line connecting NH to the ring symbolizes, according to whether a racemic or optically active agent of formula (m) has been used, a mixture of isomers or one or other of the isomers respectively, subjecting the latter to hydrogenolysis of the alkylamino to obtain a compound of the formula

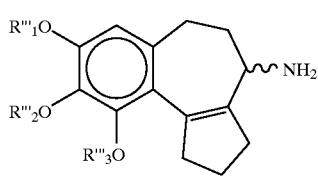   o in which the wavy line is defined as above, the amino being protected with a bivalent protective group to obtain a compound of the formula

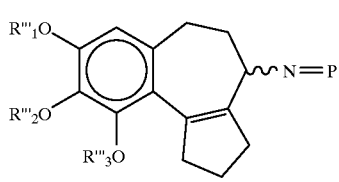   p in which the wavy line is defined as above and P is the remainder of a bivalent protective group, and the wavy line has the meaning indicated above, reacting a compound of formula n with a hydrolysis agent of $R'''_1O$ to obtain a compound of the formula

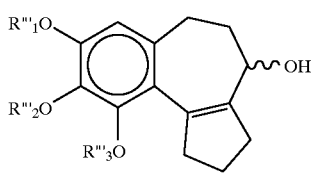

in which the wavy line between the nitrogen and the ring with 7 members indicates that this product consists of, according to the reducing agent used, either an α- or β-isomer, or a mixture of α-+β-isomers, which mixture is optionally resolved, then either reacting the alcohol with an agent of the formula HN=P, in which P has the meaning given previously to obtain a compound of the formula

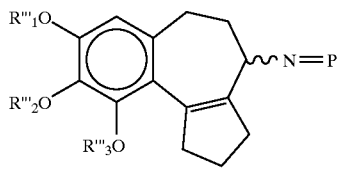

in which the wavy line between the nitrogen and the ring with 7 members indicates that the product consists of an α- or β-isomer, or a racemic mixture of isomers, or reacting the alcohol with a reagent of formula $ASO_2Hal$, in which A is defined as above and Hal is halogen to obtain the compound of the formula

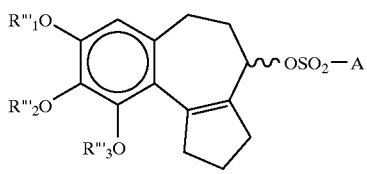

in which the wavy line and A have the above meanings, reacting the latter with ammonia to obtain the compound of formula o above, the amino group of which is protected with a bivalent protective group to obtain the compound of formula p above, then, (v) reacting a compound of formula p or q with a bromination agent in the presence of a compound of the formula $R_7OH$, in which $R_7$ is hydrogen or alkyl of 1 to 6 carbon atoms to obtain a compound of the formula

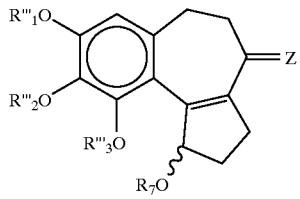

in which the wavy line indicates that the bond can be found in α- or β-position or that this product can consist of a mixture of isomers and in which =Z is =N〜$OR_8$ or

as defined in formulae p and q above, (vi) reacting the latter with a dehydration or a dealkoxylation in an anhydrous acid medium to obtain a compound of the formula

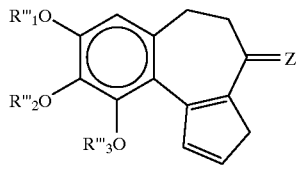

(vii) reacting the latter in the presence of a base or a metal reducing agent with an agent of the formula

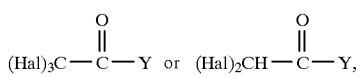

in which Hal is halogen and Y is defined as above to obtain a compound of the formula

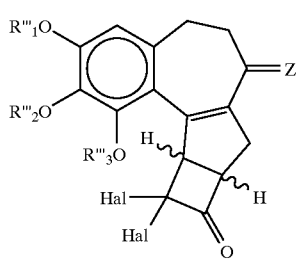

in which the wavy lines indicate that the hydrogen atoms are both found in the α-position or are both found in the β-position;

(viii) reacting the latter with an acid in the presence of a base and in an aqueous medium to obtain a compound of formula v, which exists in equilibrium with its tautomer v'

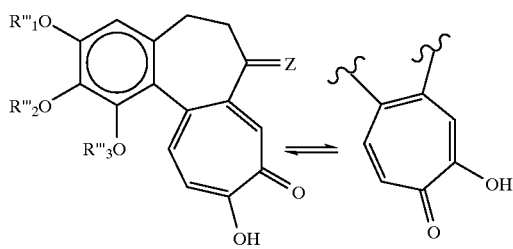

which compound, either, (ix) if =Z is

as defined above, is subjected to a deprotection reaction of the amino to obtain either the free amine of formula (w), which exists in equilibrium with its tautomer w':

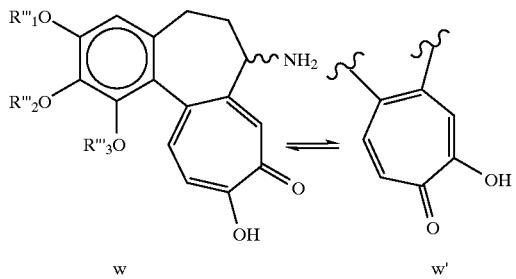

w                    w' in which the wavy line indicates that the $NH_2$ is found in the α- or β-position, or that the product consists of a mixture of isomers, reacting the latter with a reagent of the formula $R_{11}$—C(O)Y or $(R_{11}CO)_2O$, in which $R_{11}$ is alkyl of 1 to 6 carbon atoms and Y is defined as above to obtain a compound of the formula

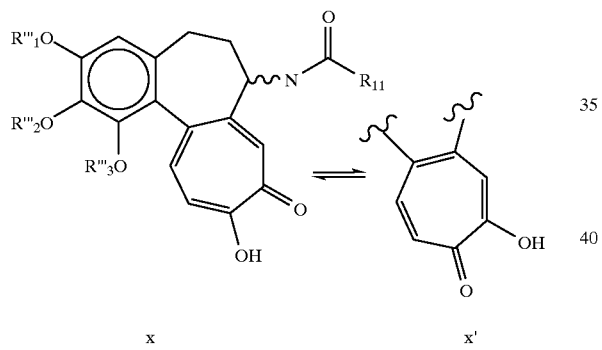

x                    x' in which the wavy line has the previous meaning, or subjecting the compound to a deprotection reaction of the amino and to a hydrolysis agent of $R'''_1$ in the case where $R'''_1$ is A—$SO_2$ as defined above to obtain a compound of the formula

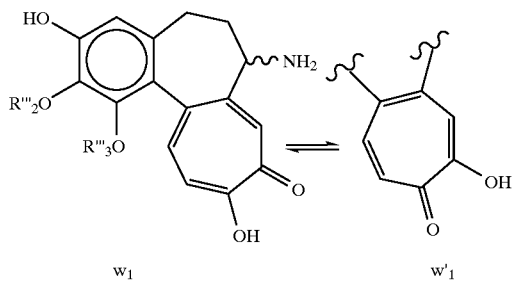

$w_1$                    $w'_1$ reacting the latter with a compound of formula $R_{11}C(O)Y$ or $(R_{11}CO)O$ as defined above to obtain a compound of the formula

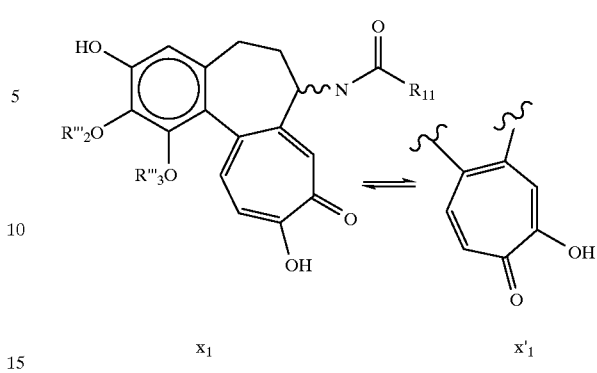

$x_1$                    $x'_1$ protecting the OH function of the latter with a reagent of the formula $ASO_2Y$ as defined above to obtain a corresponding compound of formula (x)/(x') as defined above, or, if =Z is =$N^-OR_8$, either reacting the compound with a protective agent of the formula $B(Hal)_3$ or $B(OR_4)_3$ in which $R_4$ and Hal are as defined previously, then to the action of a reducing agent to obtain a compound of the formula

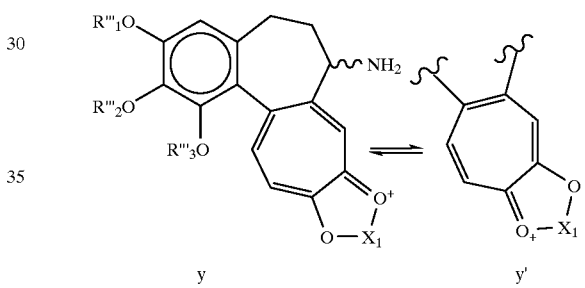

y                    y' in which the wavy line indicates that the product consists of a mixture of isomers, and $X_1$ is —$B(OR_4)_2$— or —$B(Hal)_2$ and reacting the latter with a compound of the formula $R_{11}C(O)Y$ or $(R_{11}CO)_2O$, as defined above and then to the action of a deprotection reagent of the α-hydroxy ketone to obtain a compound of formula $x''/x''_1$ corresponding to the product of formula x/x' as defined above, in which the wavy line indicates that the product consists of a mixture of isomers; reacting the compound of formula x or x' with an agent capable of introducing K defined above to obtain a compound of the formula

II

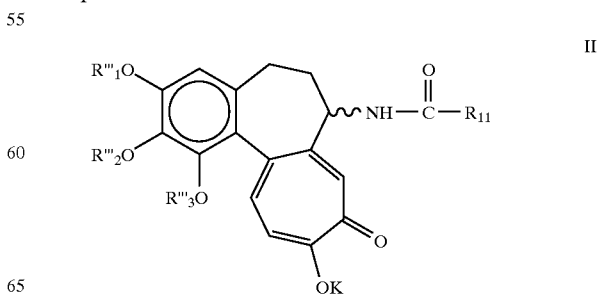

which exists in a mixture with its regioisomer of formula:

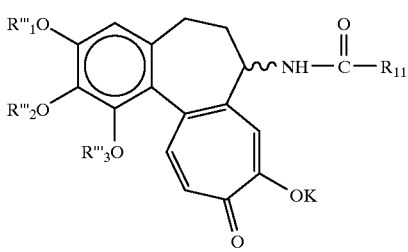

II' in which the wavy line indicates that the group is found in α- or β-position, or consists of a mixture of isomers and the terms $R'''_1$, $R'''_2$, $R'''_3$, $R_{11}$, K and alkyl have the meanings given previously, the constituents of which mixture are separated.

The reaction of the compound of formula I with the agent of formula m is preferably effected in the presence of titanium tetrachloride and a base, particularly a tertiary amine, or in the presence of an acid catalyst, particularly silica or sulfonic acid such as APTS. The preferred agent m is α-methyl-benzylamine, but norephedrine or norpseudoephedrine can also be used.

The reducing agent which is reacted on the imine intermediate is preferably a hydride such as sodium borohydride or aluminium-lithium hydride or diisobutylaluminium hydride. Hydrogen in the presence of a catalyst such as palladium or platinum can also be used. The hydrogenolysis of the alkylamino is carried out using hydrogen in the presence of a catalyst such as palladium or platinum.

The bivalent protective group of the amine is preferably phthalimido obtained by the action of phthalic anhydride or a derivative of orthophthalic acid of the formula

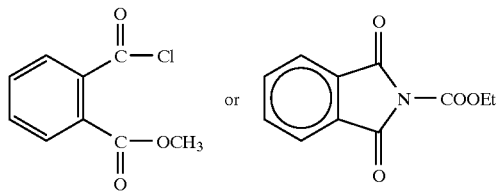

on the compound o or o', in a solvent such as toluene in the presence of a base, for example a nitrogenous base such as triethylamine. The protective group can also be maleimide, preferably diphenylmaleimide.

The hydrolysis of $R'''_{10}$ can be carried out by the action of sodium hydroxide, potassium hydroxide or sodium or potassium carbonate, in the presence of an aqueous alkanol, when $R'''_1$ is $A-SO_2-$ or by the action of a dealkylation agent such as boron tribromide, aluminium chloride, hydrochloric acid or also a mercaptan such as thiophenol when $R'''_1$ is alkyl.

The protection reagent which is reacted-with the compound of formula p' can be a known standard alkylation agent for the alkylation of phenols chosen from those indicated above or an agent of the formula $A-SO_2Y$ as defined above. The agent of formula $R_8O-NH_2$ is hydroxylamine or an alkylated derivative, for example methylhydroxylamine, and is preferably used in the form of a salt, particularly the hydrochloride.

The reducing agent for the preparation of the alcohol r is preferably a hydride such as one of those mentioned above. The alcohol is then obtained in the form of a mixture of isomers. A chiral reduction can be carried out with a chiral oxazaborolidine by the so-called Corey method. The resolution of the alcohol can be carried out by standard methods known to one skilled in the art. For example, the operation can be carried out by an enzymatic route using a lipase in the presence of vinyl acetate in an organic solvent, for example an ether such as terbutyl methyl ether.

The reagent of the formula HN=P is preferably phthalimide or a maleimide such as diphenylmaleimide. The operation is carried out in the presence of triphenylphosphine and an alkyl azodicarboxylate of the formula $R_8O_2C-N=N-CO_2-R_{10}$, where $R_8$ and $R_{10}$ are individually alkyl. The reagent of formula $ASO_2Hal$ which is reacted with the alcohol of formula r is preferably methane or p-toluene sulfonyl chloride. The compounds of formulae o and p are obtained in an inverse configuration to that of the starting alcohol of formula r.

The bromination agent is preferably pyridinium perbromide, bromine, N-bromo succinimide or dibromo dimethylhydantoin. The compound of the formula $R_7$—OH is water or preferably a lower alkanol, for example methanol or ethanol.

The compound of formula t is obtained by the action of a strong acid such as hydrochloric acid, sulfuric acid, p-toluene sulfonic acid or a sulfonic acid resin under anhydrous conditions, on the compound of formula s.

The reagent of formula $Hal_3C-C(O)-Y$ or $Hal_2CH-C(O)-Y$ is preferably tri or dichloro or dibromo acetyl chloride or bromide. The operation is carried out in the case of $Hal_2CH-C(O)-Y$ in the presence of a base, preferably a tertiary amine such as triethylamine or pyridine, under anhydrous conditions. In the case of $Hal_3C-C(O)-Y$, the operation is carried out in the presence of a metal reducing agent such as zinc and a mixture of diastereoisomers is obtained.

The rearrangement into tropolone is carried out by the action of a carboxylic acid in the presence of a base which can be an aminated base, for example triethylamine, or an alkali metal hydroxide in the presence of water and a solvent miscible in water such as acetone, dioxane or tetrahydrofuran. A product is obtained in the form of an equilibrium between the two tautomers.

The deprotection of the amine is carried out by the action of hydrazine preferably used in the form of the hydrate. The reagent of formula $R_{11}$—C(O)Y or $(R_{11}CO)_2O$ is preferably a derivative of acetic acid, for example acetyl chloride or bromide or acetic anhydride.

The selective hydrolysis of $R'''_1$ is preferably carried out by the action of an alkali metal thioalcoholate such as sodium thiomethylate in a solvent such as dimethylformamide or dimethylsulfoxide. Sodium hydroxide or potassium hydroxide, or sodium or potassium carbonate, in an alcohol such as methanol or ethanol, can also be used.

The reagent of formula $ASO_2Y$ is preferably a halide such as mesyl or tosyl chloride or bromide or also a benzyl derivative such as benzyl mesylate or tosylate. The reagent forming the protective group of the hydroxy and ketone functions of the compound $x_1/x'_1$ is boron trifluoride, trichloride or tribromide, or trimethyl or triethyl borate. The reducing agent which is reacted with the intermediate oxime is a metal such as zinc in the presence of a sulfonic acid or carboxylic acid, such as methane sulfonic acid or acetic acid.

The deprotection of the hydroxy and ketone functions is carried out by acid or basic hydrolysis or by a salt such as sodium or potassium acetate, or sodium or potassium carbonate or bicarbonate in an alcohol such as methanol or ethanol and in the presence of water.

The agent capable of introducing the K group is for example an alkyl halide such as methyl or ethyl iodide, an alkyl sulfate, such as methyl or ethyl sulfate, diazomethane, a benzyl halide such as benzyl chloride or bromide, benzyl mesylate or tosylate, or one of the reagents of formula $ASO_2Y$ mentioned previously.

The separation of the constituents of the mixture of compounds II and II' is carried out by methods known to a man skilled in the art, in particular by chromatography.

A subject of the invention is also a process as defined previously, characterized in that a compound of formula v/v' as defined previously, in which Z is

is reacted with an agent capable of introducing the K group as defined previously to obtain a compound of the formula

III

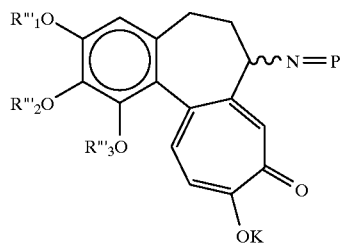

which exists in a mixture with its regioisomer of formula

III'

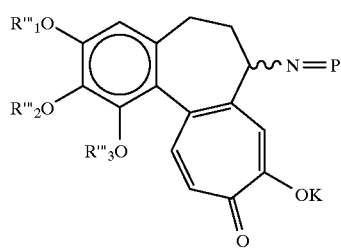

in which the wavy line indicates that the group is found in α- or β-position, or a mixture of isomers and $R'''_1, R'''_2, R'''_3$, $R_{11}$, K and alkyl have the meanings given previously, the constituents of which mixture optionally are separated, then the mixture or the separate constituents are subjected to a deprotection reaction of the amino function to obtain either a compound of the formula

IV

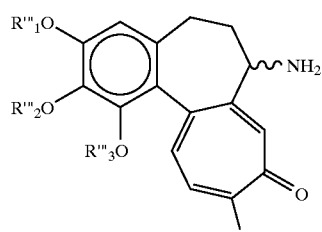

in the form of a mixture with its regioisomer of formula

IV'

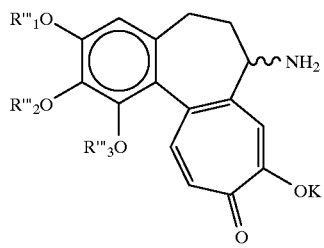

which mixture is optionally separated, or one or other of these regioisomers, then the mixture or the separate constituents are reacted with a compound of formula $R_{11}C(O)Y$ or $(R_{11}CO)_2O$, as defined above to obtain either the compound of formula II as defined above, in a mixture with its regioisomer of formula II', which mixture is optionally separated into its constituents, or one or other of these regioisomers.

In the above process, the agent capable of introducing K, the deprotection reagent of the amino function and the compounds of formula $R_{11}C(O)Y$ and $(R_{11}CO)_2O$ are the same as those which have been defined above. The separation of the various regioisomers can be carried out by methods known to one skilled in the art, particularly chromatography.

A subject of the invention is also a process as defined previously, characterized in that a compound of formula v/v' as defined previously, in which z is $=N—OR_8$, is subjected to the action of an agent capable of introducing K to obtain a compound of the formula

V

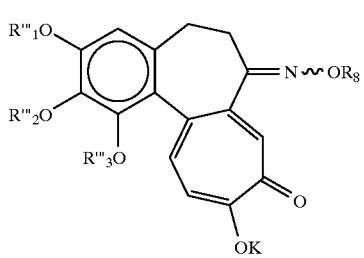

which exists in a mixture with its regioisomer of formula

V'

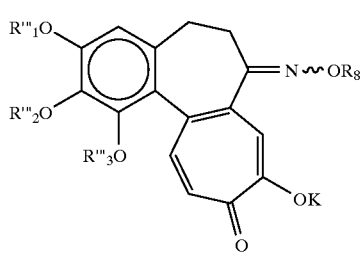

in which the wavy line, $R_8$ and $R'''_1, R'''_2, R'''_3$, K and alkyl have the above meanings, the constituents of which mixture are, optionally separated, then reacting the mixture or the separate constituents with a reducing agent to obtain either the compound of the formula

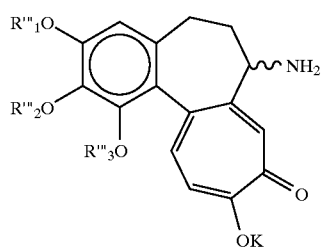

IV₁ in the form of a mixture with its regioisomer of the formula

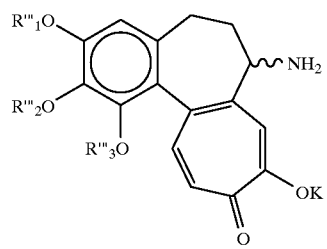

IV'₁ the wavy line symbolizing a mixture of isomers, which mixture of regioisomers optionally is separated, or one or other of these regioisomers, then the synthesis is continued as described previously for the compounds of formula IV/IV'.

In the above process, the agent capable of introducing K and the reducing agent of the oxime are the same as those which have been defined above. The separation of the regioisomers can be carried out by methods known to a man skilled in the art, particularly chromatography.

The compound of formula II in which $R'''_1$, $R'''_2$ and $R'''_3$ are methyl, K is methyl, $R_{11}$ is methyl and the wavy line symbolizes one or other isomer or a mixture of isomers, corresponds to optically active colchicine or to racemic colchicine respectively.

In a modification of the process of the invention in addition a product of the formula

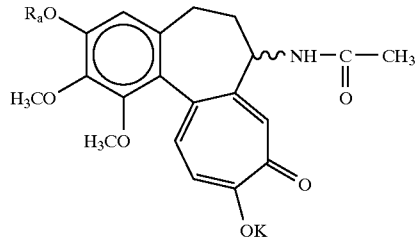

II₁ in which K is defined as previously, $R_a$ is $ASO_2$— as defined previously and the wavy line symbolizes one or other isomer or a mixture of isomers is subjected to the action of a reagent of the formula $CH_3S^-Na^+$ to obtain a compound of the formula

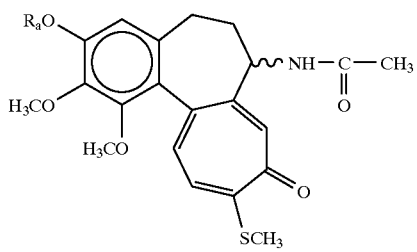

VI in which $R_a$ and the wavy line have the previous meaning, reacting the latter with a deprotection reagent of hydroxy to obtain the optically active or racemic compound of the formula

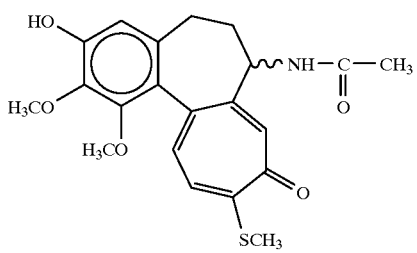

VII

The reaction with the sodium salt of methylmercaptan was preferably carried out in dimethylformamide or dimethylsulfoxide. The deprotection reagent of hydroxy is also preferably the sodium salt of methylmercaptan, the conditions used then correspond to the use of an excess of reagent.

The compound of formula VII is a compound known under the name "thio substance C" or also "desmethylthiocolchicine".

Another modification of the process is characterized in that in addition a compound of the formula

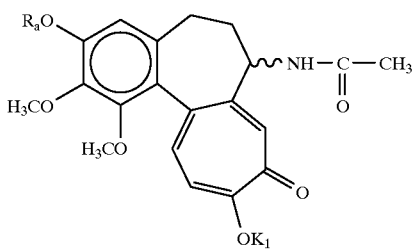

II₂ in which $R_a$ is defined as previously, $K_1$ is methyl and the wavy line symbolizes one or other isomer or a mixture of isomers is subjected to the action of a deprotection agent of hydroxy to obtain the optically active or racemic compound of the formula

VIII

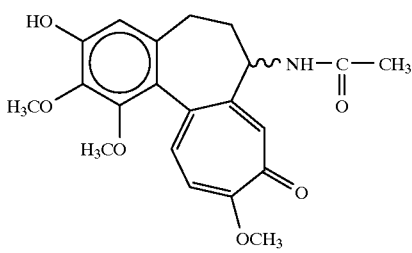

The deprotection reagent of hydroxy is one of those which have been mentioned above within the scope of obtaining the compound of formula (f). The compound of formula VIII is a compound known under the name of "substance C" or also "desmethylcolchicine".

Another modification of the process is characterized in that in addition a compound of the formula

II₃

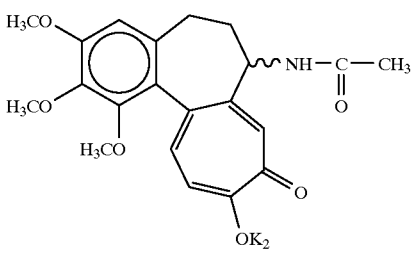

in which $K_2$ is benzyl optionally substituted on the phenyl by 1 to 3 alkyls, or —$SO_2A'$ as defined previously and the wavy line symbolizes one or other isomer, or a mixture of isomers, is subjected to the action of a reagent of the formula $CH_3S^-Na^+$, to obtain the optically active or racemic compound of the formula

IX

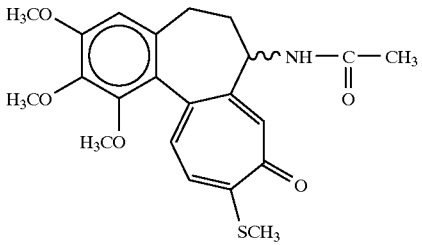

The reaction conditions are identical to those which have been mentioned above. The compound of formula IX is a compound known under the name of thiocolchicine (see for example French Patent 1,099,138).

Another variation of the process is characterized in that in addition a compound of the formula

II₄

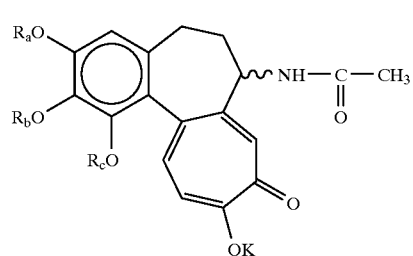

in which $R_a$ and K are defined as previously, $R_b$ and $R_c$ form together $CR_5R_6$ as defined previously and the wavy line symbolizes one or other isomer or a mixture of isomers, is subjected to the action of a deprotection reagent of the diol to obtain a compound of the formula

X

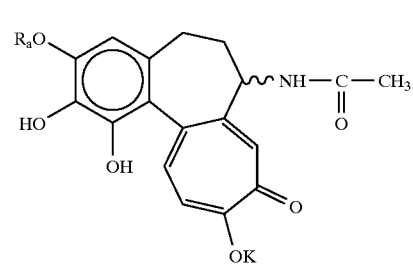

in which $R_a$, K and the wavy line have the previous meaning which is treated with a methylation agent to obtain a compound of formula $II_1$ as defined previously, then the synthesis is continued as described previously starting with said compound of formula $II_1$.

The deprotection reagent of the diol can be one those which have been mentioned above within the scope of obtaining the compound of formula k.

A further variation of the process is characterized in that in addition a compound of the formula

II₅

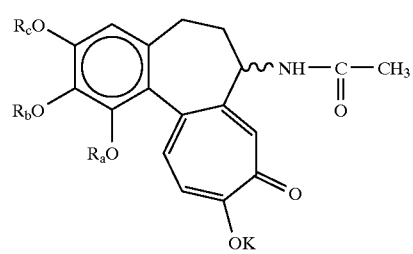

in which $R_a$, $R_b$, $R_c$, K and the wavy line are defined as in formula $II_4$, is subjected to the action of a deprotection agent of the diol, to obtain a compound of the formula

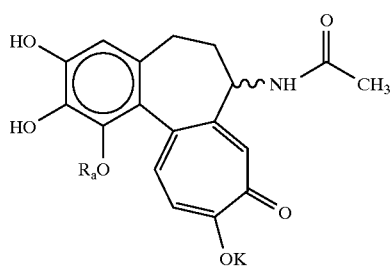

XI in which $R_a$, K and the wavy line have the previous meaning, which is subjected to the action of a hydrolysis agent to obtain the compound of the formula

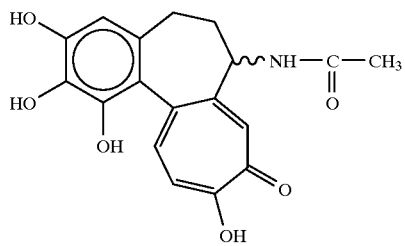

XII which is subjected to a methylation agent to obtain the optically active or racemic colchicine.

An object of the invention is also the intermediate compounds as follows:

1) The compounds of the formula

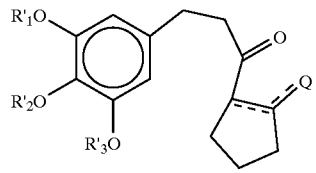

$F_1$ in which either Q is oxo, or the dotted line in the ring is a second bond and Q is halogen, $R'_1$, $R'_2$ and $R'_3$ have the meaning indicated above.

2) The compounds of the formula

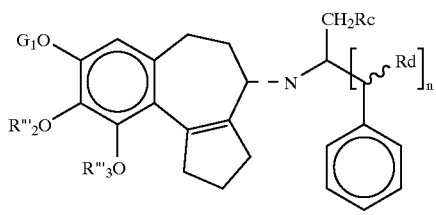

$F_2$ in which $G_1$ is hydrogen or $R'''_1$ as defined above and Rd as well as $R'''_2$ and $R'''_3$ have the meaning indicated above, the dotted line symbolizes either a double bond, or a single bond and, in this case, the nitrogen carries a hydrogen atom and the compound is in the form of a mixture of (R, S) isomers or an (R) or (S) isomer.

3) The compounds of the formula

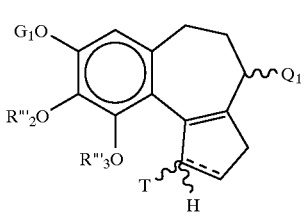

$F_3$ in which $R'''_2$ and $R'''_3$ have the meaning indicated above, and either $G_1$ is $R'''_1$ as defined previously and:

either $Q_1$ is $NH_2$ of (R), (S) or (R,S) configuration and T is hydrogen;

or $Q_1$ is N=P of (R), (S) or (R,S) configuration, P being defined as above, and either T is hydrogen or hydroxy or alkoxy containing 1 to 6 carbon atoms, of (R), (S) or (R,S) configuration, or the dotted line is a second bond;

or $Q_1$ is N~~~OR in which $R_8$ has the meaning indicated above and the wavy line indicates that the bond can be syn or anti or that the product can consist of a mixture of syn and anti isomers and either T is hydrogen or hydroxy or alkoxy containing 1 to 6 carbon atoms, of (R), (S) or (R,S) configuration, or the dotted line is a second bond;

or $Q_1$ is OH or $OSO_2A$, A being defined as above, of (R), (S) or (R,S) configuration and T is hydrogen, or $G_1$ is hydrogen atom and $Q_1$ is either $—NH_2$ of (R), (S) or (R,S) configuration, or N=P of (R), (S) or (R,S) configuration, P being as defined above and T is hydrogen, the dotted line is not a double bond.

4) The compounds of the formula

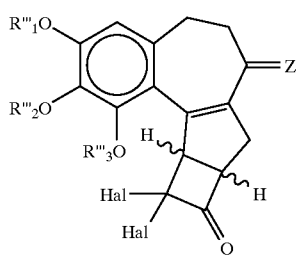

u in which $R'''_1$, $R'''_2$, $R'''_3$, Hal and Z are as defined above.

5) The compounds of the formula

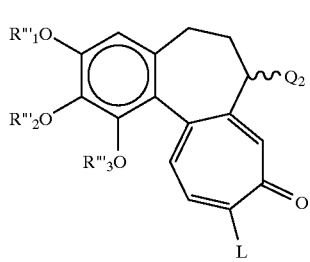

$F_4$ as well as their tautomers or regioisomers of the formula

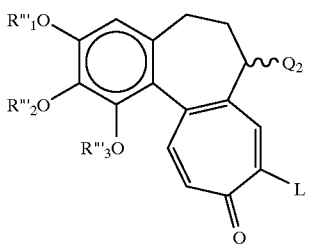

in which R'''₁, R'''₂ and R'''₃ have the meaning indicated above and ⌇⌇Q₂ is either a =N⌇⌇OR₈ as defined above and L is hydroxy, or ⌇⌇N=P group in which P has the meaning indicated above, the wavy line indicates that this group is found in (R), (S) or (R,S) configuration and L is hydroxy or -OK as defined above, with the exception of the compounds in which R'''₁, R'''₂ and R'''₃ are alkyl, L is hydroxy or alkoxy and P is =C-phenyl or CH₃—C—OC₂H₅;

or

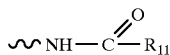

group in which R₁₁ has the meaning indicated previously, the wavy line indicates that this group is found in (R), (S) or (R,S) configuration and L is hydroxy or —OK as defined previously, with the exception of the compounds in which R'''₁, R'''₂ and R'''₃ are alkyl and L is hydroxy, alkoxy or —SO₂—A';

or ⌇⌇NH₂ of (R), (S) or (R, S) configuration and L is hydroxy with the exception of the compounds in which R'''₁, R'''₂ and R'''₃ are alkyl;

or ⌇⌇NH₂ of (R, S) configuration and L forms with the oxygen of the ketone in position 9, an O—X₁—O⁺ group as defined above, or ⌇⌇NH₂ group of (R), (S) or (R, S) configuration and L is OK as defined above, with the exception of the compounds in which R'''₁, R'''₂ and R'''₃are alkyl and K is alkyl;

or =N⌇⌇OR₈ group as defined above and L is OK as defined above.

6) The compounds of the formula

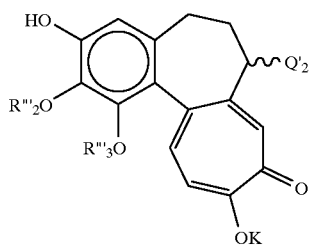

as well as their tautomers of formula:

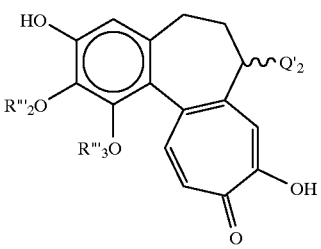

in which R'''₂ and R'''₃ have the meaning indicated above, with the except on of alkyl and ⌇⌇Q'₂ is either ⌇⌇NH—CO—R₁₁ group in which R₁₁ has the meaning indicated above, or ⌇⌇NH₂ group of (R), (S) or (R, S) configuration.

7) The compounds of the formula

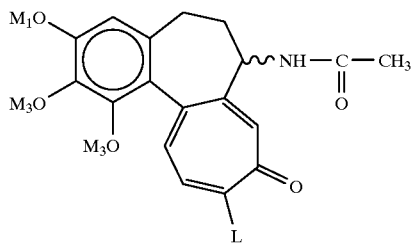

in which the wavy line indicates that the substituent is found in (R), (S) or (R,S) configuration and either M₁ and M₂ is hydroxy, M₃ is Ra as defined above and L is OK, K being as defined above, or M₂ and M₃ are hydroxy, M₁ is Ra as defined above and L is OK as defined above, or M₁ is Ra as defined above, M₂ and M₃ are methyl and L is thiomethyl.

In the following examples, there are described several preferred embodiments to illustrate the invention. However, it should be understood that the invention is not intended to be limited to the specific embodiments.

EXAMPLE 1

2,3,5,6-tetrahydro-8,9,10-trihydroxy-benz[e]-azulen-4(1H)-one

Stage A: 3,4,5-trimethoxy-benzenepropanoic acid 6.8 g of potassium carbonate were added to a solution of 21.44 g of 3,4,5-trimethoxyphenylpropenoic acid and 45 ml of water and the mixture was hydrogenated for one hour under a pressure of 1200–1300 mbar in the presence of 1.8 g of activated charcoal with 10% of palladium during which 2.1 liters of hydrogen were absorbed. Filtration was carried out, followed by washing with water and acidifying with 50 ml of hydrochloric acid (2 N). The product was separated off, washed with water and dried under reduced pressure at ambient temperature to obtain 19.8 g of the expected product melting at 102–103° C.

IR Spectrum (CHCl₃)

Carbonyl: {1712 cm⁻¹ (max), 1740 cm⁻¹ (sh)}  aromatic: {1592 cm⁻¹, 1510 cm⁻¹}

-continued

NMR Spectrum (CDCl$_3$)

| | |
|---|---|
| 2.69 (t) } =C—CH$_2$—CH$_2$—CO | 3.83 (s)} 3 H$_3$CO—C— |
| 2.91 (t) } \| | 3.85 (s)} |
| 6.43 (s) aromatic 2H's | |
| 10.50 (m) mobile 1H | |

Stage B: 3,4,5-trimethoxy-benzenepropanoyl-chloride

A solution of 6 g of the product of Stage A in 21 ml of methylene chloride was dried with 1.5 g of magnesium sulfate, and after filtration, the reaction medium was cooled to 5° C. 2.2 ml of thionyl chloride were added and the solution was stirred for 20 hours at ambient temperature and evaporated to dryness under reduced pressure by proceeding with two entrainments with cyclohexane to obtain 6.46 g of the expected product melting at 60° C.

Stage C: 2-[3-(3,4,5-trimethoxyphenyl)-1-oxopropyl]-cyclo-pentanone

A solution of 4.27 g of the product of Stage B in 15 ml of methylene chloride was added over 90 minutes at +5° C. to a solution cooled to 5° C. of 2.4 ml of 1-(N-morpholinyl) cyclopentene obtained as described hereafter, 2.31 ml of triethylamine and 15 ml of methylene chloride. The mixture was stirred for one hour at +5° C. and then while allowing the temperature to rise, 10 ml of 2 N hydrochloric acid were added. The mixture was stirred for one hour at ambient temperature, followed by decanting, washing with water, then with a saturated solution of sodium bicarbonate, drying, filtering and evaporating to dryness under reduced pressure to obtain 5 g of the expected product. The crude product was purified by dissolution in 10 volumes of ethyl acetate and extraction was carried out with a N solution of sodium hydroxide. The alkaline phase was washed with ethyl acetate, followed by acidifying to a pH of 1 with concentrated hydrochloric acid, extracting with methylene chloride, drying and evaporating to dryness under reduced pressure to obtain 2.75 g of the purified product.

IR Spectrum (CHCl$_3$): Carbonyl: {1741 cm$^{-1}$ aromatic: {1592 cm$^{-1}$ {1709 cm$^{-1}$ {1509 cm$^{-1}$ Carbonyl: {1658 cm$^{-1}$ +C=C {~1610 cm$^{-1}$ with OH in the chelated form NMR Spectrum (CDCl$_3$) 6.41 (s) arom. 2H (integration base) 3.81 (s) 3.82 (s)} 9H in all 3.83 (s) 3.85 (s)} 4 types of

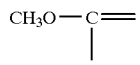

1.86 (m) CH$_2$—CH$_2$—CH$_2$ ~1.5H 1.95 to 2.95 (m) ~7.5H in all of which =C—CH$_2$ of several types 3.26 (t) ~0.4H

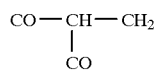

11.2 (wide m) mobile H

Preparation of 1-(N-morpholinyl)-cyclopentene used in Stage C

A solution of 100 ml of cyclohexane, 20 ml of cyclopentanone, 50 ml of morpholine and 100 mg of p-toluene sulfonic acid was stirred for 4 hours, 30 minutes at reflux, while eliminating the water formed. After evaporation of the solvent under reduced pressure, distillation was carried out under 12–13 mbar pressure to obtain 27.44 g of the expected product with a boiling point of 83° C.

Stage D: 1-(2-chloro-1-cyclopenten-1-yl)-3-(3,4,5-trimethoxy-phenyl)-propan-1-one 13 ml of oxalyl chloride were added at ambient temperature to a solution of 23 g of the product of Stage C and 230 ml of chloroform and the mixture was stirred for three hours at ambient temperature, and concentrated under reduced pressure by proceeding with two entrainments with cyclohexane to obtain 28 g of crude product which was crystallized from a mixture of 50 ml of cyclohexane and 50 ml of diisopropyl ether after partial concentration. Separation was carried out, followed by washing with diisopropyl ether and drying under reduced pressure to obtain 16.24 g of the expected product melting at 93° C.

IR Spectrum (CHCl$_3$): 1659 cm$^{-1}$: Carbonyl 1599 cm$^{-1}$ 1586 cm$^{-1}$: C=C+aromatic 1508 cm$^{-1}$ NMR Spectrum CDCl$_3$ 1.93 (m): central CH$_2$ 2.69 (m)–2.81 (m): C—CH$_2$— C= of the cyclopentene 2.85 (t, j=7.5) –3.08 (t, j=7.5): the other =C—CH$_2$—C's 2.44: CH$_3$—C= 3.68–3.81: the OCH$_3$'s 6.59–6.68 (d, j=2): paired meta aromatic CH='s 7.31–7.80 (d, j=8): the aromatics.

Stage E: 2,3,5,6-tetrahydro-8,9,10-trimethoxy-benz[e] azulen-4(1H)-one 900 mg of the product of Stage D, 9 ml of 1,2-dichloroethane and 0.9 ml of stannic chloride were stirred for 20 hours at ambient temperature. 9 ml of water and ice were added and decanting was carried out, followed by washing with water, reextracting once with methylene chloride, drying the extracts over magnesium sulfate, filtering and evaporating to dryness under reduced pressure, to obtain 1 g of the expected (crude) product which was purified by chromatographing on silica, eluting with cyclohexane with 10% of ethyl acetate, then with 25% of ethyl acetate. After concentration, 700 mg of product were collected which was crystallized from 5 ml of n-hexane, then cooled to 0° C., followed by separating, washing with the minimum of n-hexane and drying under reduced pressure at ambient temperature to obtain 630 mg of the expected product melting at 101–102° C.

NMR Spectrum (CDCl$_3$)

| | |
|---|---|
| 1.86 (m) the central CH$_2$ | |
| 2.65 (dd) 2H } | 3.84} |
| 2.72 (t) 2H } the other CH$_2$'s | 3.86} the OMe's |
| 2.84 (dd) 2H } | 3.90} |
| 3.06    2H } | |
| 6.59 (s) aromatic H | |

Stage F: 2,3,5,6-tetrahydro-8,9,10-trihydroxy-benz[e] azulen-4(1H)-one

Using the procedure of Stage F (c) of Example 2, the expected demethylated product was obtained.

EXAMPLE 2

Alternative Synthesis of: 2,3,5,6-tetrahydro-8,9,10-trihydroxy-benz[e]azulen-4(1H)-one Stage A: 3,4-dimethoxy-5-[[(4-methylphenyl)-sulfonyl] oxy]benzenepropanoic acid Using the procedure of Stage A of Example 1, 29.76 g of 3,4-dimethoxy-5-[[[(4-methylphenyl)-sulfonyl]oxy] phenyl]-cinnamic acid whose preparation is given hereafter, 43.5 g of potassium carbonate, 60 ml of methanol and 1.48 g of 10% palladium on activated charcoal were reacted to obtain 28.23 g of the desired product in the form of colorless crystals melting at 148–149° C.

UV Spectrum (EtOH) For M=380.4 max 226 nm ε=22100 infl 263 nm ε=2000 infl 269 nm ε=2400 max 274 nm ε=2800 infl 279 nm ε=2500 infl 307 nm ε=450 NMR spectrum (CDCl$_3$)

2.45 (s) CH₃—
2.61 (m) =C—CH₂—CH₂—C=   3.68 (s) 2 CH₃O—C=
2.86 (m)                  3.81 (s)
6.61 (d, j = 2)           7.32 (wd) H₃ H₅
6.65 (d, j = 2) H₄ H₆     7.80 (wd) H₂ H₆

Stage B: 3,4-dimethoxy-5-[[(4-methylphenyl)-sulfhonyl]-oxy]-benzenepropanoyl chloride Using the procedure of Stage B of Example 1, 1.9 g of the product of Stage A, 9.5 ml of methylene chloride and 0.7 ml of thionyl chloride were reacted to obtain 2.24 g of the expected product which was used as is for the following stage.

Stage C: 2-[3-[3,4-dimethoxy-5-[[(4-methylphenyl)-sulfonyl]-oxy]-phenyl]-1-oxopropyl]-cyclopentanone Using the procedure of Stage C of Example 1, 2.24 g of the acid chloride of Stage B and 770 mg of 1-(N-morpholinyl)-cyclopentene (prepared in Stage C of Example 1), 6 ml of methylene chloride and 0.77 ml of triethylamine were reacted to obtain after crystallization from diisopropyl ether, 1.27 g of the expected product melting at 84° C. IR Spectrum (CHCl₃)

| Carbonyl:      | {1742 cm⁻¹  | O—SO₂ {1374 cm⁻¹ |
|                | {1709 cm⁻¹  | {1178 cm⁻¹       |
|                | {1658 cm⁻¹  |                  |
| C=C + aromatic | {1608 cm⁻¹  |                  |
|                | {1599 cm⁻¹  |                  |
|                | {1586 cm⁻¹  |                  |
|                | {1508 cm⁻¹  |                  |

NMR Spectrum (CDCl₃) 2.44 (s) CH₃—O 3.67 (s) } 2 OCH₃ 3.79 (s) 3.81 (s)} 6.59 to 6.65 (m) arom. 2H in ortho position of the O's. 7.32 (wd) H₃ H₅ 7.89 (wd) H₂ H₆ 13.58 (wide m) enol form OH 1.8 to 3.4 (m) 10 to 11 H other protons UV Spectrum 1-EtOH (+dioxane) for M=446.52 max 225 nm ε=23000 max 282 nm ε=7900 infl 270, 277, 290, 300, 313 nm 2-EtOH (NaOH 0.1 N) max 310 nm ε=21600 infl 268, 272, 276 nm Stage D: 1-(2-chloro-1-cyclopenten-1-yl)-3-[3,4-dimethoxy-5-[[(4-methylphenyl)sulfonyl]oxy]-phenyl]-propan-1-one Using the procedure of Stage D of Example 1, 8.7 g of the product of Stage C, 70 ml of chloroform and 3.5 ml of oxalyl chloride were reacted to obtain after crystallization from diisopropyl ether, 7.75 g of the expected product melting at 73° C. This product was used as is for the following stage.

An analytical sample was obtained by crystallization from 2.5 volumes of methylene chloride and 5 volumes of diisopropyl ether followed by concentration to 3 volumes, separating, washing with diisopropyl ether and drying under reduced pressure at ambient temperature to obtain the product melting at 77–78° C.

IR Spectrum (CHCl₃) Carbonyl: {1659 cm⁻¹ Aromatic C=C: {1599 cm⁻¹ {1586 cm⁻¹ {1508 cm⁻¹ UV Spectrum (EtOH) max 227 nm ε=26100 infl 248 nm ε=12800 infl 272 nm ε=5300 infl 280 nm ε=3200 infl 320 nm NMR Spectrum (CDCl₃) 1.93 (m) central —C—CH₂—C—} 2.69 (m)} the C—CH₂—C='s} 2.81 (m)}} 2.85 (t, j=7.5)} the other =C—CH₂—C's 3.08 (t, j=7.5)} 2.44 CH₃—C= 3.68} the OCH₃'s 3.81} 6.59 (d, j=2) the aromatic CH's 6.68 (d, j=2) paired meta 7.31 (d, j=8)} 7.80 (d, j=8)}

Stage E: 8,9-dimethoxy-10-[[(4-methylphenyl)-sulfonyl]-oxy]-2,3,5,6-tetrahydro-benz[e]azulen-4(1H)-one 1.65 g of 98% ferric chloride were added at ambient temperature to a solution of 2.32 g of the product of Stage C in 50 ml of 1,2-dichloroethane and the mixture was stirred for 48 hours at ambient temperature, then poured into a water and ice mixture. The mixture was vigorously stirred for 15 minutes followed by extraction with methylene chloride, washing with water, then with a saturated aqueous solution of sodium chloride. After drying and evaporation to dryness under reduced pressure, 2.15 g of the crude product were obtained which was chromatographed, eluting with cyclohexane with 50% of ethyl acetate to obtain 1.8 g of product which was chromatographed again and crystallized from a chloroform/diisopropyl ether mixture to obtain 720 mg of the expected product melting at 138° C.

IR Spectrum (CHCl₃) Carbonyl: {1650 cm⁻¹ {1599 cm⁻¹ C=C+{1556 cm⁻¹ aromatic {1512 cm⁻¹ {1498 cm⁻¹ UV Spectrum (EtOH) max 230 nm ε=25300 infl 254 nm ε=9400 max 323 nm ε=10300 NMR Spectrum (CDCl₃) ˜1.61 (m) (2H) central CH₂ ˜2.41 Ph—CH₃ ˜2.50 to 2.80

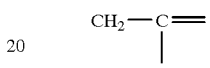

3.88 (s)} the OCH₃'s 3.90 (s)} 6.74 H4 7.21 (d)} C—PH—SO₂ 7.64 (d)}

Stage F (a): 8,9-dimethoxy-10-hydroxy-2,3,5,6-tetrahydro-benz[e]azulen-4(1H)-one A mixture of 350 g of the product of Stage E, 1,750 ml of methanol, 350 ml of demineralized water and 350 ml of pure sodium hydroxide was refluxed for 2 hours. The reaction medium was cooled to 2° C.±2° C. and 467 ml of concentrated hydrochloric acid were introduced over 45 minutes while maintaining the temperature at 2° C.±2° C. 1,645 ml of demineralized water were then added over 10 minutes and while maintaining the temperature at 2° C.±2° C., the reaction mixture was stirred for 30 minutes at 2° C.±2° C. The crystals formed were separated out, washed by clarifications 5 times with 700 ml of demineralized water each time at 20° C., then dried at 40° C. under reduced pressure to obtain 199.1 g of the expected product.

Stage F (b): 2,3,5,6-tetrahydro-8,9,10-trimethoxy-benz[e]azulen-4(1H)-one 60 g of the product of (a), 600 ml of 1,2-dichloroethane, 342 ml of 2 N sodium hydroxide, 1.2 g of tetrabutyl-ammonium bromide and 33 ml of dimethyl sulfate were stirred for 2 hours 30 minutes at 20° C. 39 ml of triethylamine were then introduced to destroy the excess dimethyl sulfate and the mixture was stirred for one hour at 20° C.±2° C. 342 ml of demineralized water were added, and the mixture was stirred for 15 minutes at 20° C.±2° C., followed by decanting, reextracting the aqueous phase twice with 120 ml of 1,2-dichloroethane each time. The 1,2-dichloroethane phases were combined and washed 4 times with 240 ml of demineralized water, then once with 300 ml of N hydrochloric acid, then 3 times with 240 ml of demineralized water (until neutrality). The combined organic phases were dried over sodium sulfate, filtered and concentrated at ordinary pressure at 83° C. until a residual volume of 480 ml was obtained.

Stage F (c): 2,3,5,6-tetrahydro-8,9,10-trihydroxy-benz[e]azulen-4(1H)-one 480 ml of the solution of (b) were heated at reflux for one hour with 102.3 g of anhydrous aluminum chloride. The medium was cooled to 0° C.±2° C. and then a mixture of 600 ml of demineralized water and 192 ml of pure sulfuric acid (concentrated). cooled beforehand to about 0° C. were added over two hours while maintaining the temperature of the reaction medium below 20° C. 300 ml of demineralized water were introduced over 5 minutes at 20° C.±2° C. and the mixture was stirred for 16 hours at 20° C.±2° C., followed by separation, washing twice with 60 ml of 1,2-dichloroethane each time, then with demineralized water and drying under reduced pressure to obtain 52.2 g of the expected product.

Preparation of the 3,4-dimethoxy 5-[[(4-methylphenyl)-sulfonyl]oxy]-cinnamic acid used at the start of Example 2

Stage A: methyl 3,4-dimethoxy-5-[[(4-methylphenyl)-sulfonyl]-oxy]-benzoate 303 ml of triethylamine were added over 10 minutes at ambient temperature to a stirred mixture of 200 g of methyl gallate and 2 liters of methylene chloride. After dissolution, the reaction medium was cooled to 0–5° C. and then 130 ml of dichlorodimethylsilane were added over one hour at this temperature. The mixture was stirred for 30 minutes at this temperature and while maintaining the temperature at 0–5° C., 303.2 ml of triethylamine were added over 25 minutes. Then, 227.6 g of tosyl chloride were added over 15 minutes and the mixture was stirred for one hour at 0–5° C. 200 ml of acetic acid and then 500 ml of demineralized water were added over 10 minutes with stirring while allowing the temperature to rise to 20–22° C. Stirring was effected for 15 minutes at 20° C. The methylene chloride was distilled off at a constant volume (3.3 l) under reduced pressure by replacing it with demineralized water. The mixture was stirred for 2 hours at 20° C., followed by separation and washing with demineralized water to obtain 523 g (wet weight) of methyl 3,4-dihydroxy-5-[[(4-methylphenyl)-sulfonyl]-oxy]-benzoate-(methyl-3-tosyl-gallate). The wet product was taken up in 2.17 liters of 2 N sodium hydroxide and 2.17 liters of methylene chloride. The mixture was stirred at 20° C. until dissolution and then 18 g of tetrabutylammonium bromide were added at 20° C. Then, over 15 minutes at 20° C., 237 ml of dimethyl sulfate were added and the reaction mixture was stirred for 90 minutes at 20–22° C. 78 ml of triethylamine were added at 20–22° C., and the mixture was stirred overnight at 20–22° C., then decanted and washed with 400 ml of demineralized water. 20 ml of pure acetic acid were added to the organic phase and the mixture was stirred for 15 minutes. 400 ml of demineralized water were added and decanting was carried out. The combined organic phases were concentrated to dryness, first under atmospheric pressure, then under reduced pressure at 40 mm Hg and 60° C. exterior temperature. Entrainment was carried out with 400 ml of methanol and the dry extract was taken up in 600 ml of methanol and heated at reflux until total dissolution of the product is achieved, then cooled to 0–5° C. and stirred for one hour at this temperature. After separating and washing twice with 200 ml of methanol at −10° C. and drying at 40° C. under reduced pressure, 330.4 g of methyl 3,4-dimethoxy-5-[[(4-methylphenyl)-sulfonyl]oxy]-benzoate were obtained. The crude product was purified by crystallization from 330 ml of toluene. After 2 hours of stirring at −10° C., separation was carried out, followed by washing twice with 82 ml of toluene cooled to −15° C. and drying under reduced pressure at 40° C. to obtain 230.3 g of the expected purified product.

Stage B: 3,4-dimethoxy 5-[[(4-methylphenyl)-sulfonyl]oxy]-cinnamic acid a) 600 ml of toluene were cooled to 0° C. and 202 ml of a solution of 70% Vitride$^R$ in toluene were added at 0° C. 67.6 ml of morpholine were added over one hour at 0–2° C., and the temperature was allowed to rise to 18° C. The solution was used immediately for the following stage.

b) 200 g of methyl 3,4-dimethoxy-5-[[(4-methylphenyl)-sulfonyl]oxy]-benzoate of Stage A and 1400 ml of toluene were stirred for 10 minutes at 20–22° C. until total dissolution was achieved. The solution of the reagent was added over one hour at 10° C. and stirring was continued for one hour while allowing the temperature to rise to 18° C. A solution cooled to 10° C. of 200 ml of concentrated sulfuric acid and 1000 ml of demineralized water was introduced over one hour at 10° C. and the mixture was stirred for 16 hours at 20° C. Then, the organic phase was decanted, washed 5 times with 200 ml of demineralized water, dried, filtered and washed 3 times with 100 ml of methylene chloride. The intermediate aldehyde solution obtained was used as is for following stage.

c) The intermediate aldehyde solution, 200 ml of 2-picoline, 120 g of malonic acid and 20 ml of piperidine were heated for 16 hours at 70° C.±2° C. while eliminating the methylene chloride under ordinary pressure. The reaction medium was cooled to 20–22° C., and while maintaining this temperature, a solution of 200 ml of concentrated hydrochloric acid and 400 ml of demineralized water were added over 15 minutes. The mixture was stirred for 2 hours at 20–22° C., and then cooled to 0° C. The crystals formed were separated off, washed with demineralized water and dried under reduced pressure at 40° C. to obtain 171.7 g of the expected 3,4-dimethoxy 5-[[(4-methylphenyl)-sulfonyl]oxy]phenyl]-cinnamic acid.

EXAMPLE 3

9,10-dimethoxy-8-[[(4-methylphenyl)-sulfonyl]-oxy]-2,3,5,6-tetrahydro-benz[e]azulen-4(1H)-one (a): 9,10-dihydroxy-8-[[(4-methylphenyl)sulfonyl)oxy]-2,3,5,6-tetrahydro-benz[e]azulen-4(1H)-one 30 g of 2,3,5,6-tetrahydro-8,9,10-trihydroxy-benz[e]azulen-4(1H)-one obtained in Example 1, 300 ml of tetrahydrofuran, 60 ml of triethylamine and 12.9 ml of trimethylborate were stirred for 90 minutes at 20° C.±2° C. 30 g of tosyl chloride were added and the mixture was stirred for 16 hours at 20° C.±2° C. and then over 10 minutes at 20° C.±2° C., the reaction medium was poured into a stirred mixture of 900 ml of demineralized water and 150 ml of concentrated hydrochloric acid. Then, 90 ml of tetrahydrofuran and 60 ml of methylene chloride were added and the solution was stirred for one hour at 20° C. Then, 150 ml of methylene chloride were introduced and the mixture was stirred for 15 minutes, followed by decanting and extracting twice with 75 ml of methylene chloride. The combined organic phases were washed 4 times with 150 ml of demineralized water and reextracted with 75 ml of methylene chloride. After concentration under a reduced pressure of 20 mbars until distillation no longer occurred at 50° C., 47.6 g of the expected product were obtained.

(b): 9,10-dimethoxy-8-[[(4-methylphenyl)-sulfonyl]-oxy]-2,3,5,6-tetrahydro-benz[e]azulen-4(1H)-one 47.6 g of the product of (a), 300 ml of methylene chloride, 300 ml 2 N sodium hydroxide, 0.6 g of tetrabutylammonium bromide and 30 ml of dimethyl sulfate were stirred for 16 hours at 20° C. 30 ml of triethylamine were then introduced to destroy the excess dimethyl sulfate and the reaction medium was stirred for another hour at 20° C.±2° C. Then, 150 ml of demineralized water were added and stirring was continued for 15 minutes followed by decanting. The aqueous phase was extracted twice with 75 ml of methylene chloride and the combined organic phases were washed 3 times with 120 ml of demineralized water, then 120 ml of N hydrochloric acid and 3 times with 120 ml of demineralized water. The organic phases were combined and dried over sodium sulfate. Then, 120 g of silica gel (60 Mesh) were added over one hour at 20° C.±2° C. with stirring which was continued for one hour at 20° C., followed by filtration, washing with methylene chloride and concentrating to dryness under reduced pressure at 50° C. to obtain 47.4 g of the expected product.

The crude product was purified by crystallization from 390 ml of ethanol after distillation of 90 ml of ethanol, and the mixture was stirred for 3 hours at 0° C.±2° C. After separation, washing with 30 ml of ethanol at 0° C. and then drying under reduced pressure at 40° C., 41.1 g of the expected product melting at 129° C. were obtained.

EXAMPLES 4–7

Asymmetrical Synthesis of "Thiosubstance C"

EXAMPLE 4

(S) 2-[9,10-dimethoxy-8-[[(4-methylphenyl)-sulfonyl]-oxy]-1,2,3,4,5,6-hexahydro-benz[e]azulen-4-yl]-1H-isoindole-1,3 (2H)-dione Stage A: 4-methylbenzenesulfonate of S (R*, R*) 9,10-dimethoxy-1,2,3,4,5,6-hexahydro-4-[(1-phenylethyl)-amino]-benz[e]azulen-8-ol, ethanedioate 26.25 ml of a 1 M solution of titanium chloride in 1,2-dichloroethane were added over 30 minutes at 5–9° C. to a solution of 6.8 ml of S(−)-α-methyl benzylamine in 45 ml of tetrahydrofuran and the mixture was stirred for 5 minutes. Then, 9 g of the product of Example 3 in solution in 45 ml of 1,2-dichloroethane and 14.7 ml of triethylamine were introduced over one hour, and the mixture was stirred for 30 minutes at about 10° C., then for 90 minutes while allowing the temperature to rise. The reaction medium was cooled to 10° C. and 9 ml of methanol were added over 3 minutes. Then, 2.52 g of sodium hydroboride were added over 40 minutes and the mixture was stirred one hour at 10° C., then for 16 hours at ambient temperature. 840 mg of sodium hydroboride were added and the reaction medium was stirred for another 45 minutes, cooled to 3° C. and hydrolyzed by the addition of 84 ml of N sodium hydroxide. After 10 minutes at 10° C., filtration was carried out, followed by washing with 90 ml of methylene chloride, decanting, washing with 40 ml of water and extracting with 40 ml of methylene chloride. Drying over sodium sulfate, filtrating and evaporating to dryness under reduced pressure yielded 18.3 g of crude product.

First Purification

The crude product was dissolved in 33 ml of methanol and 110 ml of diisopropyl ether and then 225 ml of N phosphoric acid were added. The mixture was stirred for 5 minutes followed by decanting and extracting with a mixture of 84 ml of N phosphoric acid and 16 ml of methanol and then 30 ml of water and washing with 90 ml of diisopropyl ether. The acid aqueous phases were combined and alkalinized using 22.5 g of sodium bicarbonate in the presence of 100 ml of ethyl acetate, followed by washing with water, drying over sodium sulfate, filtering and evaporating to dryness under reduced pressure to obtain 9.24 g of the expected product in the form of a resin with a specific rotation of $[\alpha]_D$=−124° (0.63% in methanol). The ratio of S:R diastereoisomers in position 4 (S being the sought isomer) was estimated at 85/15 by the ratio of the area of the peaks at 6.63 and 6.72 ppm of the NMR spectrum (corresponding to the $H_4$ protons).

Second Purification 7.15 g of the product obtained above were added over 20 minutes with stirring to a solution of 1.69 g of oxalic acid ($2H_2O$) and 6.75 ml of methanol. The mixture was stirred for 30 minutes, followed by separation, washing with ether with 5% methanol and drying under reduced pressure at ambient temperature to obtain 6.12 g of the oxalate of the expected product melting at 172° C. and having a specific rotation of $[\alpha]_D$=−170° (0.44% in methanol)

Stage B: 4-methylbenzenesulfonate of (S) 4-amino-9,10-dimethoxy-1,2,3,4,5,6-hexahydro-benz[e]azulen-8-ol 800 mg of the product of Stage A, 32 ml of a methanol-acetic acid mixture (2-1) and 240 mg of 20% palladium hydroxide on wet activated charcoal (50% water) were stirred for 5 hours at ambient temperature under a hydrogen atmosphere at 400 mbar. The reaction medium was filtered and washed with methanol, then concentrated to dryness under reduced pressure at 40° C. The oil obtained was taken up in 15 ml of ethyl acetate and 15 ml of a saturated aqueous solution of sodium bicarbonate, followed by decanting, washing, drying over sodium sulfate, filtering and evaporating to dryness under reduced pressure to obtain 590 mg of product which was chromatographed on silica, eluting with $CH_2Cl_2$ with 10% methanol to obtain 330 mg of the expected product with a specific rotation of $[\alpha]_D$=−133° (0.45% in methanol).

UV Spectrum in EtOH max 223 nm ϵ=30500 max 263 nm ϵ=12400 NMR Spectrum (CDCl$_3$) 2.45 (s) CH$_3$Ph ˜3.48 (m) H$_7$ 3.69 (s) 3.70 (s) 2 CH$_3$O—C= 1.61 to 2.05 (m) 6H) the CH$_2$'s and CH 2.30 to 2.75 (m) 6H} 3.05 (m) 1H} 6.75 (s) H$_4$ 7.32 and 7.81 (AA'BB') aromatic Stage C: (S) 2-[9,10-dimethoxy-8-[[(4-methylphenyl)-sulfonyl]-oxy]-1,2,3,4,5,6-hexahydro-benz[e]azulen-4-yl]-1H-isoindole-1,3(2H)-dione 2.63 g of phthalic anhydride and 1.4 ml of triethylamine were added to a solution of 4.3 g of the product of Stage B in 43 ml of toluene and then the mixture was heated for eight hours at reflux while eliminating the water formed. The mixture was cooled to 10° C. and 25 ml of water and 7 ml of hydrochloric acid (2 N) were added, followed by decanting and extracting once with ethyl acetate, washing with 10 ml of N sodium hydroxide, then with a saturated aqueous solution of sodium chloride, drying over magnesium sulfate, filtering and evaporating to dryness under reduced pressure to obtain 6.4 g of the crude product, which was dissolved in 6.5 ml of methylene chloride. Then, 6.4 g of aluminum oxide were introduced over 15 minutes, and after stirring for 5 minutes, filtration was carried out, followed by washing with methylene chloride and concentrating to dryness under reduced pressure, entrainment with methanol and evaporating to dryness. The residue was crystallized from 25 ml of methanol and the crystals were separated off, washed twice with 4 ml of methanol and dried under reduced pressure at 40° C. to obtain 4.42 g of the expected product melting at 139° C. and having a specific rotation of $[\alpha]_D$=−66° (c=0.6% in CHCl$_3$); Yield=79%.

EXAMPLE 5

Tautomeric mixture of: (S) 2-[1,2-dimethoxy-10-hydroxy-3-[[(4-methylphenyl)-sulfonyl]-oxy]-9-oxo-5,6,7,9-tetrahydro-benzo[a]heptalen-7-yl]-1H-isoindole-1,3(2H)-dione ("Normal Form") and (S) 2-[1,2-dimethoxy-9-hydroxy-3-[[(4-methylphenyl)-sulfonyl]-oxy]-10-oxo-5,6,7,10-tetrahydro-benzo[a]heptalen-7-yl]-1H-isoindole-1,3 (2H)-dione ("iso form")

Stage A: (4S) 2-[1,2,3,4,5,6-hexahydro-8-[[(4-methylphenyl)-sulfonyl]-oxy]-1,9,10-trimethoxy-benz[e] azulen-4-yl]-1H-isoindole-1,3(2H)-dione: Isomers (1R) and (1S)

4.45 ml of pyridine were added to a solution cooled to 5° C. of 7.7 g of the product of Example 4 in 77 ml of methylene chloride and 77 ml of methanol and then 5.28 g of pyridinium perbromide hydrobromide were added all at once. The reaction medium was stirred for three hours at 5° C. and was poured into ice-cooled water and acidified using 55 ml of N hydrochloric acid. Extraction was carried out with methylene chloride and the extracts were washed with water containing a small amount of sodium thiosulfate (to eliminate the excess oxidizing agent), then with water, dried over sodium sulfate, filtered and concentrated to dryness under reduced pressure to obtain 8.6 g of the crude product which was chromatographed on silica and eluting with methylene chloride with 5% ethyl acetate to obtain 4.38 g of diastereoisomer A ($[\alpha]_D$=−76° at 0.5% in $CHCl_3$) and 666 mg of diastereoisomer B melting at 168° C. and $[\alpha]_D$=−37° at 0.7% in $CHCl_3$) after crystallization from methylene chloride/diisopropyl ether.

Diastereoisomer A (majority product)

NMR Spectrum ($CDCl_3$)

| | |
|---|---|
| 1.93 (m)} $CH_2$ in position 9 | 2.21 (m) 1H in position 6 |
| 2.16 (m)} | 2.50 (m) 1H in position 5 |
| 2.20 (m) 1H} | |
| 2.81 (m) 1H} $CH_2$ in position 8, and other H's in positions 5 and 6 | |
| 2.93 (m) 1H} | |
| 3.18 (m) 1H} | |
| 2.45 (s) $CH_3$—Ph | |
| 3.20 (s) $OCH_3$ in position 10 | |
| 3.73 (s) $OCH_3$ in position 1 | |
| 3.75 (s) $OCH_3$ in position 2 | |
| 4.84 (m) $H_7$ | |
| 5.10 (m) $H_{10}$ | |
| 6.84 (s) $H_4$ | |
| 7.33 and 7.81 (AA'BB') -pPh—$SO_2$ | |
| 7.72 and 7.83 (m) 4H phthalimide | |

Diastereoisomer B (minority product)

NMR Spectrum ($CDCl_3$) 1.81 (m)} $CH_2$ in position 9 2.22 (m)} 2.12 (m)} $CH_2$ in position 6 2.19 (m)} 2.24 (m)} $CH_2$ in position 8 2.45 (m)} 2.44 (s) $CH_3$—Ph 2.61 (dd, j=7 and 14)} $CH_2$ in position 5 2.83 (dd, j=10 and 14)} 3.16 (s) $OCH_3$ in position 10 3.74 (s) $OCH_3$ in position 2 3.77 (s) $OCH_3$ in position 1 5.11 (dd, j=8.5 and 11.5) $H_7$ 5.24 (m) $H_{10}$ 6.72 (s) $H_4$ 7.30 and 7.79 (AA'BB') —pPh—$SO_2$ 7.69 and 7.78 (m) 4H phthalimide Stage B: (S) 2-[9,10-dimethoxy-8-[[(4-methylphenyl)-sulfonyl]-oxy]-3,4,5,6-tetrahydro-benz[e]azulen-4yl]-1H-isoindole-1,3(2H)-dione 4.1 g of the product (diastereoisomer A) of Stage A, 82 ml of methylene chloride and 205 mg of p-toluene sulfonic acid were stirred for three hours at ambient temperature and the mixture was poured into ice-cooled water and extracted with methylene chloride. The extracts were washed with water, dried over sodium sulfate, filtered and concentrated to dryness under reduced pressure to obtain 4 g of product which was chromatographed on silica, eluant: cyclohexane/ethyl acetate 2-1 to obtain 3.34 g of the expected compound.

IR Spectrum ($CHCl_3$) Carbonyl: {1775 $cm^{-1}$ {1713 $cm^{-1}$ C═C: {1612 $cm^1$ aromatic {1599 $cm^{-1}$ {1573 $cm^{-1}$ UV Spectrum (EtOH) max 221 nm $\epsilon$=71000 max 288 nm $\epsilon$=9900 infl 233, 240, 270, 277 nm NMR Spectrum ($CDCl_3$) 2.31 (m) (1H) } ~2.67 (m) (2H) } ═C—$CH_2$ 2.71 to 3.35 (<½H)} 2.46 (s) (3H) integration base the Me—Ph's 3.65 (s) 3.68 (s) 3.69 (s) the Ph—OMe's 3.74 (s) 3.76 (s) (6H in all) 5.08 (t) (⁻⅓H)} $H_7$ ~5.30 (dt) (⁻½H)} 6.33 (dd) } CH═CH—$CH_2$ other ═CH or 6.46 (d) (⅓H)) Ph—CH═C═ 6.60 (s) } 6.79 (s)} (1H in all) the $H_4$'s 6.82 } 7.35 (d) (2H)} para phenyl ~7.83} ~7.73 (m) (2H) and 7.84 (2H) phthalyl Stage C: Mixture of: (7S) 2-[10,10-dichloro-1,2-dimethoxy-3-[[(4-methylphenyl)sulfonyl]oxy]-5,6,7,8,8a,9,10,10a-octa-hydro-9-oxo-benzo[h]cyclobuta[a]azulen-7-yl]-1H-isoindole-1,3(2H)-dione and its diastereoisomer at the level of the cyclobuta[a]azulene condensation (Diastereoisomers A and B)

2.32 ml of dichloroacetyl chloride were added rapidly at 5° C. to a solution of 2.27 g of the product of Stage B in a mixture of 36 ml of methylene chloride and 18 ml of n-pentane and then 3.4 ml of triethylamine were added over 5 minutes. The reaction medium was stirred for three hours at 20° C. and then was poured into water and extracted with methylene chloride. The extracts were washed with water, dried over sodium sulfate, filtered and evaporated to dryness under reduced pressure to obtain 4.7 g of product which was chromatographed on silica, eluting with cyclohexane/ethyl acetate (2-1) to obtain 2.3 g of a two diastereoisomer mixture which was chromatographed again on silica, eluting with cyclohexane/ethyl acetate (75/25) to obtain 500 mg of isomer A, 942 mg of isomer B and 416 mg of the mixture of the two isomers.

Diastereoisomer A [$\alpha]_D$=−75° (0.5% in $CHCl_3$) IR Spectrum ($CHCl_3$) Carbonyl: {1808 $cm^{-1}$ aromatic+{1614 $cm^{-1}$ {1775 $cm^{-1}$ conj. system {1600 $cm^{-1}$ {1714 $cm^{-1}$ (F) {1570 $cm^{-1}$ Diastereoisomer B [$\alpha]_D$=−86° (0.5% in $CHCl_3$) IR Spectrum ($CHCl_3$) Carbonyl: {1808 $cm^{-1}$ aromatic+{1614 $cm^{-1}$ {1774 $cm^{-1}$ conj. system {1600 $cm^1$ {1714 $cm^{-1}$ (F) {1575 $cm^{-1}$ NMR Spectrum ($CDCl_3$)

| | |
|---|---|
| 2.05 to 2.26 (2H)} the $CH_2$'s | |
| 2.60 to 2.50 (4H)} | |
| 2.43 (s) Ph—Me | |
| 3.72 (s)} the Ph—OMe's | |
| 3.83 (s)} | |
| 4.15 (m)} CO—CH—$CH_2$ | 5.11 (dd) $H_7$ |
| 5.21 (d)} | 6.84 (s) $H_4$ |
| 7.70 to 7.83 (6H)} Ph—$SO_2$ | |
| 7.29 (d)    (2H)} | |

Stage D: Tautomeric mixture of: (S) 2-[1,2-dimethoxy-10-hydroxy-[[(4-methylphenyl)sulfonyl]oxy]-9-oxo-5,6,7,9-tetrahydro-benzo[a]heptalen-7-yl]-1H-isoindole-1,3(2H)-dione ("normal" form) and (S) 2-[1,2-dimethoxy-9-hydroxy-3-[[(4-methylphenyl)sulfonyl]oxy]-10-oxo-5,6,7,10-tetrahydro-benzo[a]heptalen-7-yl]-1H-isoindole-1,3 (2H)-dione ("iso" form)

260 mg of diastereoisomer A of Stage C, 13 ml of acetone with 20% water, 0.75 ml of glacial acetic acid and 1.8 ml of triethylamine were stirred for 72 hours at ambient temperature and the reaction mixture was poured into a water and ice mixture and extracted with methylene chloride. The extracts were washed with water, dried over sodium sulfate, filtered and concentrated to dryness under reduced pressure to obtain 244 mg of the expected product.

EXAMPLE 6

(S) N-[1,2-dimethoxy-3,10-bis[[(4-methylphenyl) sulfonyl] oxy]-9-oxo-5,6,7,9-tetrahydro-benzo[a]heptalen-7-yl]-acetamide ("normal" form) and (S) N-[1,2-dimethoxy-3,9-bis[[(4-methylphenyl)sulfonyl]oxy]-10-oxo-5,6,7,10-tetrahydro-benzo[a]heptalen-7-yl]-acetamide ("iso" form)

Stage A: (S) 7-amino-1,2-dimethoxy-3-[[(4-methylphenyl)-sulfonyl]oxy]-10-hydroxy-5,6,7,9-tetrahydro-benzo[a]-heptalen-9-one ("normal form")+"iso" tautomer 614 mg of the product of Stage D of Example 5 in solution in a mixture of 10 ml of chloroform, 10 ml of methanol and 55 μl of hydrazine hydrate were stirred for 5 hours at reflux and the reaction medium was evaporated almost to dryness. The residue was taken up in methylene chloride, filtered and the filtrate was concentrated to dryness under reduced pressure to obtain 600 mg of the expected product.

Stage B: (S) N-[1,2-dimethoxy-10-hydroxy-3-[[(4-methylphenyl) sulfonyl]oxy]-9-oxo-5,6,7,9-tetrahydro-benzo[a]heptalen-7-yl]-acetamide ("Normal Form")+"Iso" Tautomer 600 mg of the product of Stage A were dissolved in a mixture of 2.4 ml of acetic anhydride and 3.4 ml of pyridine and then the reaction medium was stirred for 16 hours at 20° C. Water was added and the mixture was stirred for 15 minutes. Then, the reaction medium was poured into N hydrochloric acid and extraction was carried out with methylene chloride. The extracts were washed with water, dried over sodium sulfate, filtered and evaporated to dryness under reduced pressure to obtain 600 mg of the expected product.

Stage C: (S) N-[1,2-dimethoxy-3,10-bis[[(4-methylphenyl) sulfonyl]oxy]-9-oxo-5,6,7,9-tetrahydro-benzo[a]heptalen-7-yl]-acetamide ("normal" form) and (S) N-[1,2-dimethoxy-3,9-bis[[(4-methylphenyl)sulfonyl]oxy]-10-oxo-5,6,7,10-tetrahydro-benzo[a]heptalen-7-yl]-acetamide ("Iso" form)

A mixture of 1.5 g of the product of Stage B, 570 mg of tosyl chloride, 455 mg of sodium bicarbonate, 15 ml of methylene chloride, 15 ml of water and 75 mg of tetrabutylammonium hydrogen sulfate was stirred for 2 hours 30 minutes. The mixture was decanted, washed with water, dried over sodium sulfate, filtered and evaporated to dryness under reduced pressure to obtain 2.01 g of tosylated product. The tautomeric forms of which ("normal" and "iso" forms) were fixed by this acylation. The product, which consisted of a mixture of the two tosylated isomers, was crystallized by dissolution in 6 ml of ethyl acetate and crystallization by the addition of 6 ml of diisopropyl ether, followed by separation and washing with an ethyl acetate-diisopropyl ether mixture (1/1). After drying under reduced pressure at ambient temperature, 1.76 g of the expected product were obtained (isomer mixture, ratio of "normal"/"iso" forms: 68/32).

Separation of the isomers by chromatography 1.75 g of the mixture of the two isomers above were chromatographed on silica by eluting with methylene chloride with 15% acetone. The fractions containing the "iso" isomer were concentrated to dryness to obtain 515 mg of product which was suspended in 6 ml of a diisopropyl ether/ethyl acetate mixture (2:1). Separation was carried out, followed by washing with diisopropyl ether and drying under reduced pressure at ambient temperature to obtain 499 mg of the "Iso" product in the form of colorless crystals; (Dec. ~205° C.). $[a]_D$=−171° (0.28% in CHCl$_3$).

The fractions containing the "Normal" isomer were concentrated to dryness to obtain 1.11 g of product which was crystallized from 12 ml of diisopropyl ether/ethyl acetate (2:1). Separation was carried out, followed by washing with diisopropyl ether and drying under reduced pressure at ambient temperature to obtain 1.07 g of the "normal" product (Dec. 197° C.). $[a]_D$=−147° (0.39% in CHCl$_3$).

Isolation of the "normal" isomer by alkaline treatment

The "normal" isomer sought was obtained by alkaline treatment of the mixture of the two "normal"/"iso" tosylated tautomers, which brought about the specific degradation of the "iso" product which was not sought.

3 g of the mixture of the two tosylated isomers of Stage C, suspended in 15 ml of methanol and 4.4 ml of 2 N lithium hydroxide, were stirred for 90 minutes. Separation was carried out, followed by washing twice with 7.5 ml, then once with 5 ml of water, and drying under reduced pressure at ambient temperature to obtain 1.94 g of the "normal" isomer. $[\alpha]_D$=−145° (at 0.46% in CHCl$_3$).

Examination of the "normal" isomer obtained by chromatographic separation

IR Spectrum (CHCl$_3$) ~3440 cm$^{-1}$ =C—NH 1684 cm$^{-1}$ Carbonyl 1626 cm$^{-1}$) other Carbonyl 1599 cm$^{-1}$) aromatic C=C 1585 cm$^{-1}$) Amide II 1514 cm$^{-1}$} 1496 cm$^{-1}$}

EXAMPLE 7

(S) N-[1,2-dimethoxy-3-hydroxy-10-methylthio-9-oxo-5,6,7,9-tetrahydro-benzo[a]heptalen-7-yl]-acetamide (Thiosubstance C)

Preparation of sodium mercaptide 8 g of sodium, 360 ml of tetrahydrofuran and 19.5 ml (216 mmoles) of dimethyl disulfide were stirred for 47 hours at 35–40° C. and the suspension was then siphoned with moderate stirring to remove the excess sodium. The solvent was evaporated off under reduced pressure, at 40° C. and 27.2 g of the product were obtained which was crystallized from diisopropyl ether, and after drying under reduced pressure, 20.36 g of sodium mercaptide were obtained. 1 g of the product of Stage C of Example 6 ("normal" isomer) was added at 20° C. over three minutes to a mixture of 520 mg of sodium mercaptide and 5 ml of dimethylformamide, and the mixture was stirred for one hour at ambient temperature. Then, a mixture of 6 ml of water, 4 ml of 2 N hydrochloric acid at 0° C. and then 10 ml of ethyl acetate were added, followed by decanting, drying over sodium sulfate, filtering and evaporating to dryness under reduced pressure. After crystallization from a mixture of ethyl acetate-diisopropyl ether (2:1), 400 mg of the expected product with a specific rotation of $[\alpha]_D$=−334° (0.26% in EtOH) and an endothermal melting point at 309° C. were obtained.

IR Spectrum (CHCl$_3$) 3525 cm$^{-1}$—OH 3440 cm$^{-1}$=C—NH 1674 cm$^{-1}$ Carbonyl 1614 cm$^{-1}$} C=O 1586 cm$^{-1}$}+1550 cm$^{-1}$) aromatic C=C 1521 cm$^{-1}$} Amide II 1498 cm$^{-1}$} NMR Spectrum 2.00 (s) NAc 2.44 (s) SMe 1.83 (m) 1H} CH$_2$ in position 5 and 6 2.15 to 2.55 3H} 3.65 (s)} the OMe's 4.01 (s)} 4.65 (m) H$_7$ 5.94 (ws) OH 6.59 (s) H$_4$ 6.93 (d) NH—C=O 7.07 (d, j=10.5)} H$_{11}$ and H$_{12}$ 7.28 (d, j=10.5)} 7.32 (s) H$_8$

EXAMPLES 8–12

Racemic Synthesis

EXAMPLE 8

O-methyloxime of 9,10-dimethoxy-8-[[(4-methyl-phenyl)sulfonyl]oxy]-2,3,5,6-tetrahydro-benz[e]azulen-4(1H)-one 1.05 g of 98% methoxylamine hydrochloride and 1.3 g of pyridine were added at 20° C. to a solution of 3.5 g of the product of Stage B of Example 3 in 17.5 ml of methylene chloride and 35 ml of methanol and the reaction medium was stirred for 16 hours at 20° C. It was poured into water, ice and an excess of 0.1 N hydrochloric acid and extraction was carried out with methylene chloride. The extracts were washed with water, dried, filtered and evaporated to dryness under reduced pressure to obtain 5 g of the expected product (mixture of syn and anti isomers of the oxime). The crude product was chromatographed on silica, eluting with methylene chloride with 5% diisopropyl ether. The purified product was concentrated to dryness and crystallized by concentration in a diisopropyl ether-methylene chloride mixture to obtain 1.4 g of pure majority isomer melting at 110° C. and 1.2 g of the mixture of syn or anti isomers at the level of the O-methyloxime group.

IR Spectrum (CHCl$_3$) of the majority isomer: Absence of carbonyl 1599 cm$^{-1}$} 1574 cm$^{-1}$} C=C 1494 cm$^{-1}$} C=N+ 1481 cm$^{-1}$} aromatic 1375 cm$^{-1}$} —OSO$_2$ 1178 cm$^{-1}$}

NMR Spectrum (CDCl₃ of the majority isomer: 1.90 (m) central CH₂ 2.45 (s) CH₃—Ph 2.60 to 3.05 the other CH₂'s 3.66 and 3.69 1 and 2 —OCH₃ 3.88 (s) =N—OMe 6.74 (s) H₄ ~7.32} —pPh—SO₂ ~7.80}

EXAMPLE 9

Tautomeric mixture of: 7-O-methyloxime of 1,2-dimethoxy-10-hydroxy-3-[[(4-methylphenyl)sulfonyl]oxy]-5,6-dihydro-benzo[a]heptalene-7,9-dione ("normal" form) and 7-O-methyloxime of 1,2-dimethoxy-9-hydroxy-3-[[(4-methylphenyl)sulfonyl]oxy]-5,6-dihydro-benzo[a]heptalene-7,10-dione ("iso" form)

Stage A: O-methyloxime of 8-[[(4-methylphenyl)sulfonyl]oxy]-2,3,5,6-tetrahydro-1,9,10-trimethoxy-benz[e]azulen-4(1H)-one, (racemized in position 1)

0.8 ml of pyridine and 1 g of pyridinium perbromide hydrobromide were added at ambient temperature to a solution of 1.14 g of majority isomer of Example 8 in 12.5 ml of methylene chloride and 12.5 ml of methanol. After stirring for 24 hours at 20° C., the reaction medium was poured into a mixture of water, ice and an excess of N hydrochloric acid. Extraction was carried out with methylene chloride and the extracts were washed with water containing a small amount of sodium thiosulfate, then with pure water, dried over sodium sulfate, filtered and evaporated to dryness under reduced pressure to obtain 1.2 g of the crude product which was chromatographed on silica, eluting with methylene chloride with 5% diisopropyl ether. The fractions containing only the racemic mixture of the two isomers (of position 1) of the expected product were evaporated to dryness and the product was crystallized from a diisopropyl ether/n-pentane mixture to obtain 377 mg of the expected product melting at 117° C.

IR Spectrum (CHCl₃) 1599 cm⁻¹} conjugated system and 1575 cm⁻¹} aromatic NMR Spectrum (CDCl₃) 1.79 (m)} central CH₂ 2.38 (m)} 2.45 —pPh—Me 3.22 (s) —C—OMe 3.71 (s) (6H) =C—Me 3.89 (s) (3H) =N—OMe ~2.50 to 3.15 the =C—CH₂'s 5.22 (t)

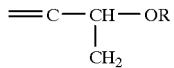

6.72 (s) H₄ 7.31 (d)} —pPh— 7.78 (d)}

Stage B: O-methyloxime of 5,6-dihydro-9,10-dimethoxy-8-[[(4-methylphenyl)sulfonyl]oxy]-benz[e]azulen-4(1H)-one 230 mg of the product of Stage B, 6.25 ml of methylene chloride and 23 mg of p-toluene sulfonic acid were stirred for two hours at ambient temperature and then was poured into a mixture of water, ice and 2 ml of a saturated aqueous solution of sodium bicarbonate. Extraction was carried out with methylene chloride and the extracts were washed with water, dried over sodium sulfate, filtered and evaporated to dryness under reduced pressure. The product obtained was chromatographed on silica, eluting with methylene chloride, followed by evaporating to dryness to obtain a product which was used as is for the following stage.

Stage C: Racemic mixture of: 7-O-methyloxime of 10,10-dichloro-1,2-dimethoxy-5,6,8,8a,10,10a-hexahydro-3-[[(4-methylphenyl)sulfonyl]oxy]-benzo[h]cyclobuta[a]azulene-7,9-dione and its diastereoisomer at the level of the cyclobuta[a]azulene condensation The product of Stage B was dissolved in 4 ml of methylene chloride and 1 ml of n-pentane and then a solution of 0.4 ml of dichloroacetyl chloride, 0.6 ml of triethylamine and 4 ml of n-pentane was added over 5 minutes. The reaction mixture was stirred for 2 hours at ambient temperature and then was poured into water and ice. Extraction was carried out with methylene chloride and the extracts were washed with water, dried over sodium sulfate, treated with activated charcoal, filtered, then evaporated to dryness under reduced pressure to obtain 700 mg of crude product which was chromatographed on silica, eluting with methylene chloride. The fractions containing only the mixture of cyclo-adducts were concentrated to dryness and the product obtained was crystallized from methanol containing a small amount of diisopropyl ether. The crystals were separated off, washed with the minimum of methanol and dried under reduced pressure at ambient temperature to obtain 89 mg of the expected product melting at 170° C.

IR Spectrum (CHCl₃) 1807 cm⁻¹ carbonyl 1599 cm⁻¹} aromatic+ 1575 cm⁻¹} C=C, C=N NMR Spectrum (CDCl₃) 2.44 (s) —pPh—Me 2.36 (m) (1H) } the CH₂—C='s 2.53 to 2.71 (2H)} 3.04 to 3.28 (3H)} 4.29 (m) (1H)}

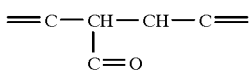

5.16 (1H)} 6.82 (s) H₄ 7.30 (d)} —pPh— 7.74 (d)} 3.71 (s)} the =C—OMe's 3.78 (s)} =N—OMe 3.88 (s)}

Stage D: Tautomeric mixture of: 7-O-methyloxime of 1,2-dimethoxy-10-hydroxy-3-[[(4-methylphenyl)sulfonyl]oxy]-5,6-dihydro-benzo[a]heptalene-7,9-dione ("normal" form) and 7-O-methyloxime of 1,2-dimethoxy-9-hydroxy-3-[[(4-methyl-phenyl) sulfonyl]oxy]-5,6-dihydro-benzo[a]heptalene-7,10-dione ("iso"form)

0.46 ml of acetic acid and 1.12 ml of triethylamine were added at 20° C. to a solution of 166 mg of the product of Stage C in 8 ml of acetone with 20% water and the reaction mixture was stirred for five days at ambient temperature, then poured into water. Extraction was carried out with methylene chloride and the extracts were washed with water, dried over sodium sulfate, treated with activated charcoal, filtered and concentrated to dryness under reduced pressure to obtain 170 mg of the expected product.

EXAMPLE 10

Tautomeric mixture of: N-[1,2-dimethoxy-3-[[(4-methylphenyl)sulfonyl]oxy]-9-oxo-5,6,7,9-tetrahydro-10-[[2,4,6-tris(1-isopropyl)phenyl]sulfonyl]oxy]-benzo[a]heptalen-7-yl]-acetamide ("normal" form), racemic at the level of position 7 of the benzo[a]heptalen nucleus and N-[1,2-dimethoxy-3-[[(4-methylphenyl)sulfonyl]oxy]-10-oxo-5,6,7,9-tetrahydro-9-[[[2,4,6-tris(1-methylethyl)phenyl]sulfonyl]oxy]-benzo[a]heptalen-7-yl]-acetamide ("iso" form), racemic at the level of position 7 of the benzo[a]-heptalene nucleus Stage A: Tautomeric mixture of: (T-4)-[7-methoxyimino-1,2-dimethoxy-10-hydroxy-3-[[(4-methylphenyl)sulfonyl]oxy]-9-oxo- 5,6,7,9-tetrahydro-benzo[a]heptalenato]difluoro-boron and (T-4)-[7-methoxyimino-1,2-dimethoxy-9-hydroxy-3-[[(4-methyl-phenyl) sulfonyl]oxy]-10-oxo-5,6,7,10-tetrahydro-benzo[a]-heptalenato]difluoro-boron 0.5 ml of trifluoroboride diethyl etherate were added at 20° C. to a solution of 1.023 g of the product of Example 9 in 2 ml of methylene chloride and 10 ml of methanol, and the mixture was stirred three hours at ambient temperature. The reaction mixture was poured into a water and ice mixture and extraction was carried out with methylene chloride. The extracts were washed with a saturated aqueous solution of sodium bicarbonate, then with water, dried over sodium sulfate, treated with activated charcoal, filtered and evaporated to dryness under reduced pressure at less than 30° C. to obtain 1.4 g of the expected crude product. The product was chromatographed on silica, eluting with methylene chloride with 5% diisopropyl ether and 0.1% triethylamine to obtain 917 mg of the expected product.

IR Spectrum (CHCl$_3$) 1608 cm$^{-1}$ } 1599 cm$^{-1}$ } C=O 1583 cm$^{-1}$) C=N 1570 cm$^{-1}$ (sh)} aromatic 1545 cm$^{-1}$ (sh)} 1495 cm$^{-1}$ (sh)} 1484 cm$^{-1}$ } 1152 cm$^{-1}$ } SO$_2$ 1179 cm$^{-1}$ UV Spectrum 1—In EtOH: for M=559.35 max 227 nm ϵ=38000 max 339 nm ϵ=14500 infl 250, 380 nm 2—In EtOH-0.1 N hydrochloric acid: max 228 nm ϵ=40700 max 339 nm ϵ=16900 max 456 nm ϵ=900 infl 250, 380 nm 3—In EtOH-0.1 N NaOH: max 258 nm ϵ=25100 max 356 nm ϵ=23100 max 410 nm ϵ=10600 NMR Spectrum (CDCl$_3$) 2.48 (s) Me—Ph 3.43 3.79 3.93 } the —OMe's 3.39 3.67 3.81 } (and 3.46 3.78)} 6.87 6.88 (and 6.95) H$_4$ 7.37 } —Ph—SO$_2$ 7.84 } 7.65 (and 7.67) 7.92 (s) H$_8$ ~7.80 } 8.11 (d, j=10.5) } H$_{11}$ and H$_{12}$ 8.19 (d, j=11.5) } (and 8.18; d, j=11.5)}

Stage B: Tautomeric mixture of: (T-4)-[7-amino-1,2-dimethoxy-10-hydroxy-3-[[(4-methylphenyl)sulfonyl]oxy]-9-oxo-5,6,7,9-tetrahydro-benzo[a]heptalenato]difluoro-boron ("Normal" Form)—racemic in position 7 and (T-4)-[7-amino-1,2-dimethoxy-9-hydroxy-3-[[(4-methylphenyl)sulfonyl]oxy]-10-oxo-5,6,7,10-tetrahydro-benzo[a]-heptalenato]difluoro-boron ("Iso" Form)—racemic in position 7

920 mg of electrolytic zinc (Vieille Montagne) and 3.4 ml of methane sulfonic acid were added to a solution of 2.83 g of the product obtained in Stage A above in 50 ml of tetrahydrofuran and the mixture was stirred 72 hours at ambient temperature. The reaction mixture was poured into a mixture of water, ice, sodium bicarbonate and methylene chloride, followed by decanting and extraction another two times with methylene chloride. The extracts were washed with water, dried over sodium sulfate, filtered and concentrated to dryness under reduced pressure to obtain 2.8 g of the expected crude product. This product was chromatographed on silica, eluting with cylcohexane-ethyl acetate: (1:1) and 1% triethylamine to obtain 1.67 g of the expected product.

NMR Spectrum (CDCl$_3$) 1.77 (m)} 2.14 (m)} the CH$_2$ s 2.38 (m)} 2.49 (m)} 2.49 (s) Me—Ph 3.58 and 3.80 the OMe's 3.94 (dd) H$_7$ 6.86 (s) H$_4$ ~7.33) —pPh—SO$_2$ ~7.87} 7.73 (d, j=11.5)} H$_{11}$ and H$_{12}$ 8.05 (d, j=11.5)} 8.82 (s) H$_8$ Stage C: Tautomeric mixture of: (T-4)-[7-acetylamino-1,2-dimethoxy-10-hydroxy-3-[[(4-methylphenyl)sulfonyl]oxy]-9-oxo-5,6,7,9-tetrahydro-benzo[a]heptalenato]difluoro-boron ("normal" form)—racemic in position 7 and (T-4)-[7-acetylamino-1,2-dimethoxy-9-hydroxy-3-[[(4-methylphenyl) sulfonyl]oxy]-10-oxo-5,6,7,10-tetrahydro-benzo[a]-heptalenato]difluoro-boron ("iso" form)—racemic in position 7

475 mg of the product of Stage B, 3 ml of pyridine and 2 ml of acetic anhydride were stirred for 48 hours at ambient temperature and the reaction medium was poured into 20 ml of slightly acidified water in the presence of methylene chloride. The mixture was stirred for 20 minutes, followed by decanting and extracting twice with methylene chloride. The extracts were washed with 2 N hydrochloric acid, then with water, dried over sodium sulfate and evaporated under reduced pressure to obtain 540 mg of dry extract which was chromatographed on silica, eluting with ethyl acetate with 1% triethylamine, to obtain 226 mg of the expected product.

NMR Spectrum (CDCl$_3$) 2.00 to 2.65 CH$_2$ in position 5 and 6 2.06 (ws) N—Ac 2.48 (s) CH$_3$—Ph 3.52 and 3.81 the =C—OMe's 4.66 (m) H$_7$ 6.77 (d) NHC=O 6.94 (s) H$_4$ ~7.38 } —pPh—SO$_2$ ~7.86 } 7.79 (d, j=11) H$_{11}$ and H$_{12}$ 8.18 (d, j=11)

Stage D: Tautomeric mixture of: N-[1,2-dimethoxy-10-hydroxy-3-[[(4-methylphenyl)sulfonyl]oxy]-9-oxo-5,6,7,9-tetrahydro-benzo[a]heptalen-7-yl]-acetamide ("normal" form), racemic at the level of position 7 of the benzo[a]heptalene nucleus and [1,2-dimethoxy-9-hydroxy-3-[[(4-methylphenyl)sulfonyl]oxy]-10-oxo-5,6,7,9-tetrahydro-benzo[a]heptalen-7-yl]-acetamide ("iso" form), racemic at the level of position 7 of the benzo[a]heptalene nucleus 200 mg of the product of Stage C in 4 ml of methanol and 0.7 ml of a 2 M aqueous solution of sodium acetate were stirred for 16 hours at ambient temperature and the reaction medium was poured into water. The precipitate was separated, washed with water and dried under reduced pressure at 20° C. to obtain 146 mg of the expected product.

Stage E: Tautomeric mixture of: N-[1,2-dimethoxy-3-[[(4-methylphenyl)sulfonyl]oxy]-9-oxo-5,6,7,9-tetrahydro-10-[[[2,4,6-tris(1-isopropyl)phenyl]sulfonyl]oxy]-benzo[a]heptalen-7-yl]-acetamide ("normal" form), racemic at the level of position 7 of the benzo[a]heptalene nucleus and N-[1,2-dimethoxy-3-[[(4-methylphenyl)sulfonyl]oxy]-10-oxo-5,6,7,9-tetrahydro-9-[[[2,4,6-tris(1-isopropyl)phenyl] sulfonyl]oxy]-benzo[a]heptalen-7-yl]-acetamide ("iso" form), racemic at the level of position 7 of the benzo[a]heptalene nucleus 1.5 ml of water, 25 mg of sodium bicarbonate, 94 mg of [2,4,6-tris(1-isopropyl)phenyl]-sulfonyl chloride and 8 mg of tetrabutylammonium hydrogen sulfate were added to a solution of 79 mg of the product of Stage D in 1.5 ml of methylene chloride and the mixture was stirred for 16 hours at 20° C. The reaction medium was poured into water and extraction was carried out with methylene chloride. The extracts were washed with water, dried over magnesium sulfate, filtered and concentrated to dryness under reduced pressure to obtain 164 mg of a mixture of expected product ("normal" form) and its regioisomer ("iso" form). After chromatography on silica (eluant: cyclohexane-ethyl acetate (1:1)), 38 mg of the "iso" isomer and 67 mg of the "normal" form isomer product expected were obtained.

IR Spectrum (CHCl$_3$) ~3440 cm$^{-1}$ =C—NH 675 cm$^{-1}$ } carbonyl 1625 cm$^{-1}$ } 1599 cm$^{-1}$ } C=C 1586 cm$^{-1}$ } aromatic 1537 cm$^{-1}$ } amide II 1514 cm$^{-1}$ } 1496 cm$^{-1}$ }

EXAMPLE 11

Tautomeric mixture of: 2-[10-hydroxy-9-oxo-5,6,7,9-tetrahydro-1,2,3-trimethoxy-benzo[a]heptalen-7-yl]-1H-isoindole-1,3(2H)-dione, racemic in position 7 of the benzo[a]heptalene nucleus and 2-[9-hydroxy-10-oxo-5,6,7,10-tetrahydro-1,2,3-trimethoxy-benzo[a]heptalen-7-yl]-1H-isoindole-1,3(2H)-dione, racemic in position 7 of the benzo[a]heptalene nucleus Stage A: 1,2,3,4,5,6-hexahydro-8,9,10-trimethoxy-benz[e] azulen-4-ol, racemic mixture at the level of position 4

757 mg of sodium hydroboride were added all at once to a solution of 5.766 g of the product of Stage E of Example 1 in 75 ml of methanol and 5 ml of methylene chloride and the reaction mixture was stirred for 16 hours at ambient temperature. The mixture was poured into water and extraction was carried out twice with methylene chloride. The extracts were washed with water, dried over sodium sulfate, filtered and concentrated to dryness. The product was taken up in methylene chloride and diisopropyl ether and concentrated to a small volume, followed by separation and washing with diisopropyl ether to obtain 5.55 g of the expected product.

Stage B: 2-[1,2,3,4,5,6-hexahydro-8,9,10-trimethoxy-benz[e]azulen-4-yl]-1H-isoindole-1,3(2H) dione, racemic mixture in position 4 of the benz[e]azulene nucleus 5.55 g of the product of Stage A and 3.327 g of diethyl azodicarboxylate and 13.5 ml of tetrahydrofuran were added with stirring to a mixture of 5 g of triphenylphosphine, 2.811 g of phthalimide and 80 ml of tetrahydrofuran and the reaction mixture was stirred for 16 hours at ambient temperature. After this time, the same quantities of triphenylphosphine, phthalimide and diethyl azodicarboxylate were added again and stirring was continued for 16 hours. Then, the reaction medium was poured into water and extraction was carried out with methylene chloride. The extracts were washed twice with water, dried over sodium sulfate, filtered and concentrated to dryness and 30 g of the product were obtained which was chromatographed on silica, eluting with a methylene chloride-ethyl acetate mixture (2:1), to obtain 6.16 g of the expected product.

Stage C: 2-[1,2,3,4,5,6-hexahydro-1,8,9,10-tetramethoxy-benz[e]azulen-4-yl]-1H-isoindole-1,3(2H) dione, racemic mixture in position 4 of the benz[e]azulene nucleus (stereochemistry in position 1 of the benz[e]azulene nucleus not established)

A suspension of 6.16 g of the product of Stage B, 62 ml of methanol and 4.75 ml of pyridine was cooled to 0° C. and then 5.64 g of pyridinium perbromide hydrobromide were added all at once. The temperature was allowed to rise and the mixture was stirred for 2 hours at ambient temperature. Then, 25 ml of methanol was added and stirring was continued for one hour. Another 0.94 g of pyridinium perbromide hydrobromide were added, and stirring was continued for 10 hours. The reaction medium was then poured into ice-cooled water bringing about a precipitation of the expected product. Methylene chloride and 29.4 ml of 2 N hydrochloric acid were added and extraction was carried out twice with methylene chloride. The extracts were washed with water, dried over sodium sulfate, filtered and concentrated to dryness to obtain 7.2 g of crude product which was chromatographed on silica, eluting with methylene chloride with 5% diisopropyl ether to obtain 2.9 g of the product. The latter was dissolved in methylene chloride and then after the addition of diisopropyl ether, the solution was concentrated to a small volume, ice-cooled and separation was carried out to obtain 2.54 g of the expected product melting at 200° C.

Stage D: 2-[10,10-dichloro-5,6,7,8,8a,9,10,10a-octahydro-9-oxo- 1,3(2H)-dione, racemic in position 7 of the benzo[h]cyclobuta[a]azulene nucleus+its diastereoisomer at the level of the cyclobuta[a]azulene condensation, (racemic in position 7 of the benzo[h]cyclobuta[a]azulene nucleus) and 2-[3,4,5,6-tetrahydro-8,9,10-trimethoxy-benz[e]azulen-4-yl]-1H-isoindole-1,3(2H) dione, racemic mixture in position 4 of the benz[e]azulene nucleus (non-isolated=diene intermediate)

a) 50 mg of p-toluene sulfonic acid were added at 5° C. to a solution of 1 g of the product of Stage C in 40 ml of methylene chloride and the mixture was stirred for 30 minutes at ambient temperature.
  b) The reaction medium was cooled to 5° and 10 ml of water and 1.62 ml of triethylamine were added. Then, 1.12 ml of dichloroacetyl chloride were added and the mixture was stirred for one hour at ambient temperature. 0.54 ml of triethylamine and 0.37 ml of dichloroacetyl chloride were then added and stirring was continued for 30 minutes. The reaction medium was poured into ice-cooled water and extraction was carried out with methylene chloride. The extracts were washed with water, dried over sodium sulfate, filtered and concentrated to dryness to obtain 2.58 g of crude product which was chromatographed on silica, eluting with methylene chloride with 5% diisopropyl ether. The fractions containing both of the two isomers of the expected product were concentrated to dryness to obtain 640 mg of the desired product which was chromatographed again eluting with methylene chloride-ethyl acetate (2:1), to obtain 59 mg of the isometrically pure minority isomer, 124 mg of the isometrically pure majority isomer and 419 mg of a mixture of the two isomers.

Stage E: Tautomeric mixture of 2-[10-hydroxy-9-oxo-5,6,7,9-tetrahydro-1,2,3-trimethoxy-benzo[a]heptalen-7-yl]-1H-isoindole-1,3(2H)-dione, racemic in position 7 of the benzo[a]heptalene nucleus and of 2-(9-hydroxy-10-oxo-5,6,7,10-tetrahydro-1,2,3-trimethoxy-benzo[a]heptalen-7-yl]-1H-isoindole-1,3(2H)-dione, racemic in position 7 of the benzo[a]heptalene nucleus 419 mg of the mixture of the two isomers of Stage D were stirred for 3 hours at ambient temperature with 8.5 ml of acetone with 20% water, 0.553 ml of acetic acid and 1.3 ml of triethylamine and then the reaction medium was poured into ice-cooled water. Extraction was carried out with methylene chloride and the extracts were washed with ice-cooled N hydrochloric acid, then with water, dried over sodium sulfate, filtered and concentrated to dryness to obtain 365 mg of the expected product.

EXAMPLE 12

2-[9-oxo-5,6,7,9-tetrahydro-1,2,3-trimethoxy-10-[[[2,4,6-tris(1-isopropyl)phenyl]sulfonyl]oxy]-benzo[a]heptalen-7-yl]-1H-isoindole-1,3(2H)-dione ("Normal" Form), racemic in position 7 of the benzo[a]heptalene nucleus 365 mg of the product of Stage E of Example 11 were stirred for 48 hours at ambient temperature with 7 ml of methylene chloride, 7 ml of water, 129 mg of sodium bicarbonate, 36.5 mg of tetrabutylammonium hydrogen sulfate and [2,4,6-tris(1-methyl-ethyl)phenyl]-sulfonyl chloride and the reaction medium was poured into ice-cooled water. Extraction was carried out with methylene chloride and the extracts were washed with water, dried over sodium sulfate, filtered and concentrated to dryness to obtain 965 mg of crude product which was chromatographed on silica, eluting with methylene chloride with 5% diisopropyl ether to obtain 151 mg of the desired product which was chromatographed a second time, eluting with methylene chloride with 5% diisopropyl ether to obtain 75 mg of the expected product.

EXAMPLE 13

4-methylbenzenesulfonate of (S) 4-amino-8,9-dimethoxy-1,2,3,4,5,6-hexahydro-benz[e]azulen-10-ol Stage A: (R) 8,9-dimethoxy-10-[[(4-methylphenyl)-sulfonyl]-oxy]-2,3,5,6-tetrahydro-benz[e]azulen-4(1H)-beta-ol 0.046 mmoles of oxaza borolidine complex (whose preparation is given hereafter) in solution in 100 μl of tetrahydrofuran were added to a solution of 200 mg of 8,9-dimethoxy-10-[[(4-methyl-phenyl)-sulfonyl]-oxy]-2,3,5,6-tetrahydro-benz[e]azulen-4(1H)-one (obtained in Stage E of Example 2) in 2 ml of tetrahydrofuran and then 0.56 ml of borane-tetrahydrofuran complex (0.88 M) were added over 15 minutes while allowing the temperature to rise to about 30° C. The reaction medium was cooled to 0° C. and 5 ml of ice-cooled water were added without exceeding 10° C. The mixture was stirred for 30 minutes and then extraction was carried out with methylene chloride. The extracts were washed with water, dried and evaporated to dryness under reduced pressure to obtain 224 mg of product which was chromatographed on silica, eluting with chloroform with 3% acetone to obtain 197 mg of the desired product.

NMR Spectrum 330 MHz (CDCl$_3$) 1.6 to 2.8: the CH$_2$'s 2.45: CH$_3$—Φ— 3.64 to 3.89: the O—CH$_3$'s 4.27 (wide):

CH$_2$—CH—OH 6.71: H$_4$ in a position of OSO$_2$—Φ 7.31 to 7.79: aromatics

Preparation of the oxazaborolinic complex used in Stage A

90 μl of trimethyl boroxine were added dropwise at ambient temperature to a solution of 250 mg of (R)-(+)-α,α-diphenyl-2-pyrrolidine-methanol in 20 ml of toluene and the mixture was stirred for 15 minutes. The toluene and the excess reagent were eliminated by distillation under reduced pressure to obtain the crystallized product which was used as is.

Stage B: 4-methylbenzenesulfonate of (S) 4-amino-8,9-dimethoxy-1,2,3,4,5,6-hexahydro-benz[e]azulen-10-ol A solution of 40 mg of the product of Stage A in 0.8 ml of methylene chloride was cooled to −55° C. and 44 μl of triethylamine were added dropwise. The mixture was stirred for 10 minutes at −55° C. and then 2.0 μl of methane sulfonyl chloride in solution in 50 μl of methylene chloride were introduced slowly. The mixture was stirred for 10 minutes at −55° C. and 0.5 ml of liquefied ammonia were added, without exceeding −50° C. The mixture was stirred for 2 hours at −50° C. and then the temperature was allowed to rise to eliminate the excess ammonia. The reaction medium was cooled to 0+5° C. and then, 2 ml of ice-cooled water were introduced with stirring for 20 minutes at this temperature, followed by extraction with ethyl acetate. The extracts were washed with water, filtered and evaporated to dryness under reduced pressure to obtain 38.3 mg of crude product which was chromatographed on silica, eluting with a toluene-methanol-ammonium hydroxide mixture (80–20–1) to obtain 24.2 mg of the desired product.

NMR Spectrum 300 MHz (CDCl$_3$) 1.5 to 2.8: the CH$_2$'s 2.44: CH$_3$—Φ— 3.70 to 3.86: the O—CH$_3$'s 3.74: CH—NH$_2$ 6.71: H$_4$ in a position of OSO$_2$—Φ 7.35 to 7.83: aromatics

EXAMPLE 14

4-methylbenzenesulfonate of (S) 4-acetyloxy-8,9-dimethoxy-1,2,3,4,5,6-hexahydro-benz[e]azulen-10-ol Stage A: (R,S) 8,9-dimethoxy-10-[[(4-methylphenyl)-sulfonyl]-oxy]-2,3,5,6-tetrahydro-benz[e]azulen-4(1H)-ol Using the procedure of Stage A of Example 11, 8,9-dimethoxy-10-[[(4-methylphenyl)-sulfonyl]-oxy]-2,3,5,6-tetrahydro-benz[e]azulen-4(1H)-one (obtained in Stage E of Example 2) was reacted to obtain the desired product.

Stage B: 4-methylbenzenesulfonate of (S) 4-acetyloxy-8,9-dimethoxy-1,2,3,4,5,6-hexahydro-benz[e]azulen-10-ol 0.81 ml of vinyl acetate and 150 mg of Lipase PS Amano were added to a mixture of 150 mg of the product of Stage A and 7.5 ml of terbutyl methyl ether. The suspension was stirred for 27 hours at ambient temperature and membrane filtration was carried out to eliminate the lipase followed by evaporating to dryness under reduced pressure to obtain 138 mg of crude product which was chromatographed on silica, eluting with chloroform with 5% acetone to obtain 65.2 mg of the desired product and 66.4 mg of non-converted product.

NMR Spectrum 300 MHz (CDCl$_3$) 1.6 to 2.8: the CH$_2$'s 2.45: CH$_3$—Φ 3.64 to 3.89: the O—CH$_3$'s 4.27 (wide): CH$_2$—CH—OH 6.71: H$_4$ in α position of OSO$_2$—Φ 7.30 to 7.79: aromatics.

EXAMPLE 15

(S) 2-[9,10-dimethoxy-8-[[(4-methylphenyl)-sulfonyl]oxy]-1,2,3,4,5,6-hexahydro-benz[e]azulen-4-yl]-1H-isoindole-1,3(2H)-dione Stage A: (S) 9,10-dimethoxy 8-hydroxy 1,2,3,4,5,6-hexahydro-4-[(1-phenylethyl)amino]benz[e]azulene 4.5 g of potassium hydroxide were added to 10 g of the product of Stage A of Example 4 in 50 ml of methanol and the mixture was heated for one hour at reflux. The solution was cooled to 20° C. and 20 ml of acetic acid, then 150 ml of water were added. Extraction was carried out with dichloromethane and after chromatography on silica, 6.4 g of the expected product were obtained.

NMR Spectrum (CDCl$_3$) ppm 6.82: mobile 2H's 6.47: H$_4$ 3.64 to 3.84: the 2 CH$_3$O's 3.3 (t): H$_7$.

Stage B: (S) 4-amino 8-hydroxy 9,10-dimethoxy 1,2,3,4,5,6-hexahydro-benz[e]azulene 5 g of the product of Stage A, 50 ml of methanol, 25 ml of acetic acid and 150 ml of water were stirred for 30 hours at ambient temperature under a hydrogen atmosphere (400 mbar) in the presence of 2 g of 20% palladium hydroxide on wet activated charcoal (50% water). Filtration was carried out followed by washing with methanol, then concentrating to dryness under reduced pressure at 40° C. After crystallization from ethyl acetate, 3 g of the expected product were obtained.

NMR Spectrum (CDCl$_3$) ppm 6.59 (s): H$_4$ 3.79 and 3.89 (2s): the 2 CH$_3$O's 3.49 (m): H$_7$ 1.6 (wide m): mobile H's.

STAGE C: (S) 2-(9,10-dimethoxy 8-hydroxy 1,2,3,4,5,6-hexα-hydro-benz[e]azulen-4-yl) 1H-isoindole-1,3(2H)-dione 0.8 g of phthalic anhydride and 2 ml of triethylamine were added to a solution of 3 g of the product of Stage B in 30 ml of toluene and then the mixture was heated for 16 hours at reflux. The reaction medium was cooled to 20° C. and washed with 20 ml of N hydrochloric acid. After decanting, washing with water and drying, the solvent was evaporated off to obtain 4.42 g of the expected product which was used as is for the following stage.

NMR Spectrum (CDCl$_3$) ppm 6.60 (s): H$_4$ 5.70: OH 5.01 (m): H$_7$ 3.82 and 3.95 (2s): the 2 CH$_3$O's 7.7 and 7.82 (2m): the aromatics.

Stage D: (S) 2-[9,10-dimethoxy-8-[[(4-methylphenyl)-sulfonyl]oxy]-1,2,3,4,5,6-hexahydro-benz[e]azulen-4-yl]-1H-isoindole-1,3(2H)-dione The product of Stage C was introduced into 45 ml of dichloromethane and 4 ml of triethylamine and 2.5 g of tosyl chloride were added. Then, the mixture was stirred for 16 hours at 20° C. and the reaction medium was washed with N hydrochloric acid, then with water, dried and crystallized from methanol to obtain 5.50 g of the expected product which was identical to that of Example 4.

EXAMPLE 16

(S) 9,10-dimethoxy 8-hydroxy 1,2,3,4,5,6-hexa-hydro 4-((1-phenylethyl)amino)-benz[e]azulene Stage A: 9,10-dimethoxy 8-hydroxy 2,3,5,6-tetrahydro-benz[e]azulen-4(1H)-one 4.5 g of potassium hydroxide, then 10 ml of triethylamine were added to a suspension of 10 g of 9,10-dimethoxy 8-(((4-methylphenyl)sulfonyl)oxy) 2,3,5,6-tetrahydro-benz[e]-azulen-4(1H)-one of Stage B of Example 3 and 100 ml of methanol. The reaction medium was heated for one hour at reflux, acidified by the addition of 20 ml of acetic acid and then 20 ml of water were added. Extraction was carried out with dichloromethane and the extracts were washed with water. The solvent was evaporated at 40° C. under reduced pressure to obtain 5.7 g of the expected product which was used as is for the following stage.

Stage B: (S) 9,10-dimethoxy 8-hydroxy 1,2,3,4,5,6-hexahydro ((1-phenylethyl)-imino)-benz[e]azulen-4-yl 5 g of silica and 6 ml of S (−) methylbenzylamine were added to 5 g of the product of Stage A in 50 ml of toluene and heating was carried out for 16 hours at reflux while eliminating the water by azeotropy. The reaction medium was filtered and the solvent was evaporated under reduced pressure to obtain 6.9 g of the expected product which was used as is for the following stage.

Stage C: (S) 9,10-dimethoxy 8-hydroxy 1,2,3,4,5,6-hexahydro 4-((1-phenylethyl)amino)-benz[e]azulene The product of Example 15 was dissolved in 700 ml of tetrahydrofuran and 2 g of palladium on activated charcoal were added. Hydrogenation (1.2 bar) was carried out for 20 hours and after filtering and evaporating the solvent, 6.9 g of the expected product were obtained which was identical to that of Stage A of Example 15.

Various modifications of the products and process of the invention may be made without departing from the spirit or scope thereof and it should be understood that the invention is intended to be limited only as defined in the appended claims.

What we claims is:

1. A process for the preparation of a compound of the formula

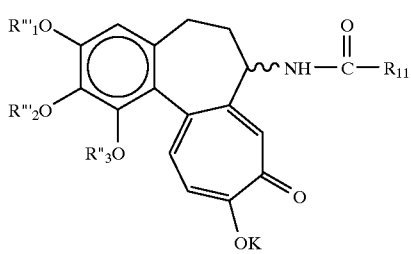

II in which a) $R_1$ and $R_2$ are alkyl of 1 to 6 carbon atoms and $R_3$ is hydrogen or A—$SO_2$— or b) $R_2$ and $R_3$ are hydrogen and $R_1$ and A—$SO_2$— or c) $R_1$, $R_2$ and $R_3$ are all hydrogen or all alkyl of 1 to 6 carbon atoms or d) $R_1$ is A—$SO_2$— or hydrogen and $R_3$ and $R_3$ together with the oxygens to which they are attached form —O—X—O—, X is selected from the group consisting of B(OR$_4$)—, C(O)— and —CR$_5$—R$_6$—, $R_4$ is hydrogen or alkyl of 1 to 6 carbon atoms, $R_5$ and $R_6$ are individually selected from the group consisting of hydrogen, alkyl of 1 to 6 carbon atoms and phenyl optionally substituted with 1 to 3 members of the group consisting of —OH and alkyl and alkoxy of 1 to 6 carbon atoms or $R_5$ and $R_6$ together with the carbon atom to which they are attached form a carbocyclic of 5 to 6 carbon atoms or e) $R_3$ is A—$SO_2$— and $R_1$ and $R_2$ together with the oxygens to which they are attached form —O—X—O— or f) $R_1$ is hydrogen and $R_2$ and $R_3$ are both alkyl of 1 to 6 carbon atoms together with the oxygens to which they are attached form —O—X—O and A is selected from the group consisting of alkyl of 1 to 6 carbon atoms, phenyl optionally substituted with 1 to 3 alkyls of 1 to 6 carbon atoms and naphthyl optionally substituted with 1 to 5 alkyls of 1 to 6 carbon atoms, $R'''_1$, $R'''_2$ and $R'''_3$ have the same meanings as the $R_1$, $R_2$ and $R_3$ groups with the exception of hydrogen, and, for $R_2$–$R_3$, X other than —CR$_5$R$_6$ and, for $R_1$–$R_2$, X other than —CR$_5$—R$_6$—, $R_{11}$ is alkyl of 1 to 6 carbon atoms, the wavy line indicates that NH—C(O)R$_{11}$ is found in α- or β-position, or that the compound is in the form of a mixture of α- or β-isomers, and K is alkyl of 1 to 6 carbon atoms, benzyl optionally substituted on the phenyl by 1 to 3 alkyls of 1 to 6 carbon atoms, or —$SO_2$—A', in which A' is chosen independently from the values of A above comprising:

(i) reacting a compound of formula I

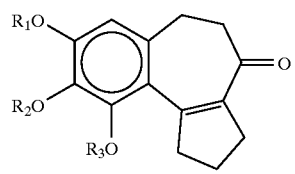

I wherein $R_1$, $R_2$ or $R_3$ are not hydrogen with an agent of the formula

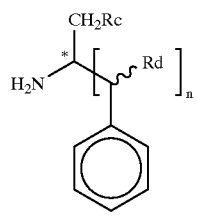

m in racemic or optically active form, in which Rc and Rd are individually hydrogen or hydroxy and n is 0 or 1: reacting the imino intermediate thus obtained with a reducing agent to obtain a compound of the formula

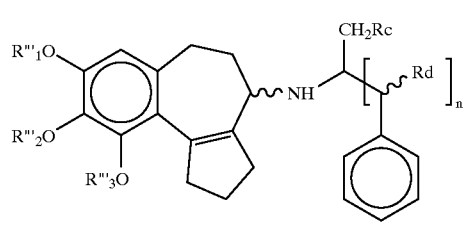

n in which Rc and Rd have the above meanings and they wavy line connecting NH to the ring symbolizes, according to whether a racemic or optionally active agent of formula (m) has been used, a mixture of isomers or one or other of the isomers respectively, either subjecting the latter to hydrogenolysis of the alkylamino to obtain a compound of the formula

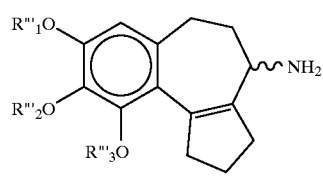

o in which the wavy line is defined as above, the amino being protected with a bivalent protective group to obtain a compound of formula

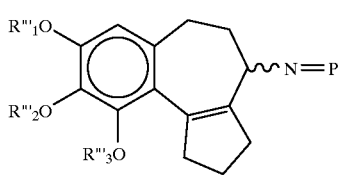
p in which the wavy line is defined as above and P is the remainder of a bivalent protective group, and the wavy line has the meaning indicated above, or reacting a compound of formula n with a hydrolysis agent of R'''₁O to obtain a compound of the formula

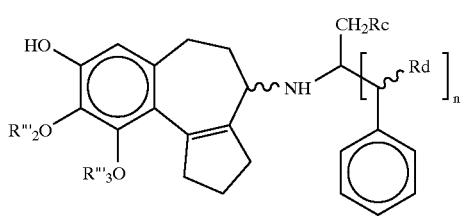
n' in which R'''2, R'''₃, R_c, R_d, n and the wavy lines have the above meaning, subjecting the latter to hydrogenolysis of the alkylamino to obtain a compound of the formula

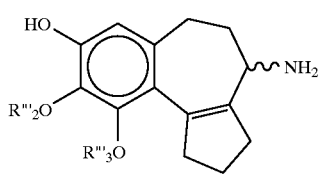
o' in which the wavy line is defined as above, the amino group being protected with a bivalent protective group to obtain a compound of the formula

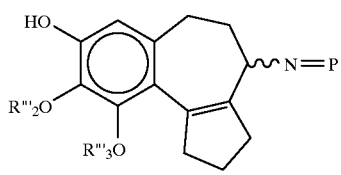
p' in which P and the wavy line have the above meaning, reacting the latter with a protective agent of the hydroxy to obtain a compound of formula (p) as defined previously;

(ii) reacting a compound of formula p with a bromination agent in the presence of a compound of the formula R₇OH, in which R₇ is hydrogen or alkyl of 1 to 6 carbon atoms to obtain a compound of the formula

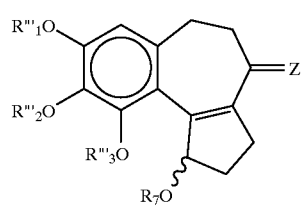
s in which the wavy line indicates that the bond can be found in α- or β-position or that this product can consist of a mixture of isomers in which =Z is

as defined in formula p above, (iii) reacting the latter with a dehydration agent or a dealkoxylation agent in an anhydrous acid medium to obtain a compound of the formula

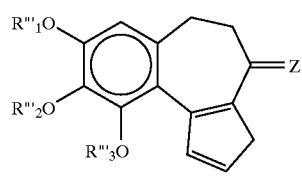
t (iv) reacting the latter in the presence of a base or a metal reducing agent with an agent of the formula

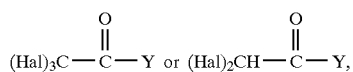

in which Hal is halogen and Y is defined as above to obtain a compound of the formula

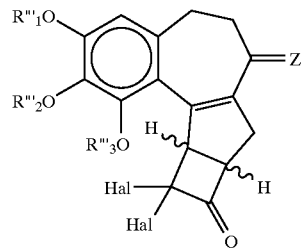
u in which the wavy lines indicate that the hydrogen atoms are both found in the α-position or are both found in the β-position;

(v) reacting the latter with an acid in the presence of a base and in an aqueous medium to obtain a compound of formula v, which exists in equilibrium with its tautomer v'

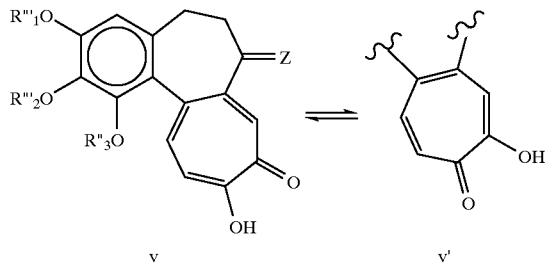

v    v' which compound is subjected to a deprotection reaction of the amino to obtain either the free amine of formula w, which exists in equilibrium with its tautomer w':

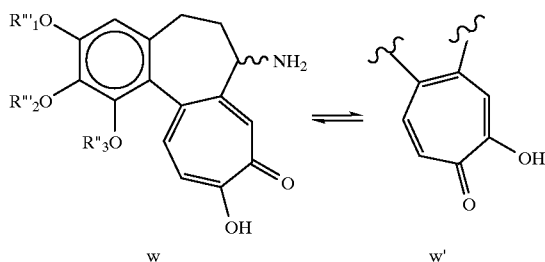

w    w' in which the wavy line indicates that the NH$_2$ is found in the α- or β-position, or that the product consists of a mixture of isomers, reacting the latter with a reagent of the formula R$_{11}$—C(O)Y or (R$_{11}$CO)$_2$O, in which R$_{11}$ is alkyl of 1 to 6 carbon atoms and Y is defined as in to obtain a compound of the formula

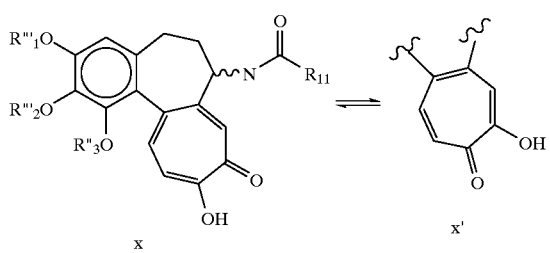

x    x' in which the wavy line has the previous meaning, or subjecting the compound to a deprotection reaction of the amino and to a hydrolysis agent of R'''$_1$ in the case where R'''$_1$ is A—SO$_2$ as defined above to obtain a compound of the formula

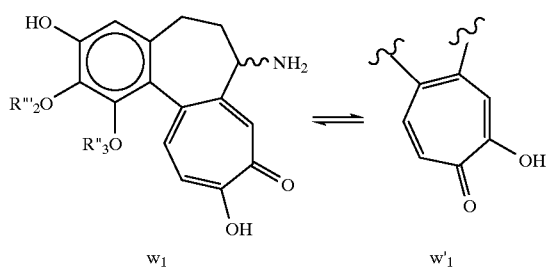

w$_1$    w'$_1$ reacting the latter with a compound of the formula R$_{11}$C(O)Y or (R$_{11}$CO)O as defined above to obtain a compound of the formula

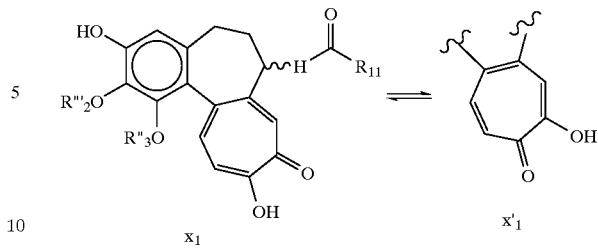

x$_1$    x'$_1$ protecting the OH function of the latter with a reagent of the formula ASO$_2$Y as defined above to obtain a corresponding compound of formula x/x' as defined above, reacting the compound of formula x or x' with an agent capable of introducing k as defined above to obtain a compound of the formula

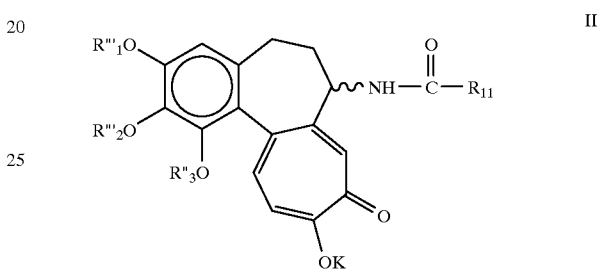

II which exists in a mixture with its regioisomer of formula:

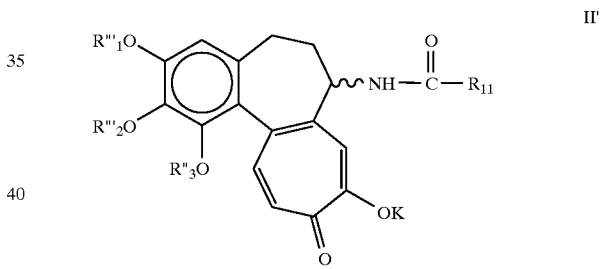

II' in which the wavy line indicates that the group is found in α- or β-position, or consists of a mixture of isomers and the terms R'''$_1$, R'''$_2$, R'''$_3$, R$_{11}$, K and alkyl have the meanings given previously, the constituents of which mixture are separated.

2. The process of claim 1 wherein the amine of formula m is selected from the group consisting of (S)-α-methyl-benzyl-amine, norephedrine and norpseudoephedrine.

3. The process of claim 1 wherein the amino protective group is phthalimido or maleimido.

4. The process of claim 1 wherein R$_7$ is methyl.

5. The process of claim 1 wherein the halogenated compound reacted with the compound t is dichloroacetyl chloride.

6. The process of claim 1 wherein R$_{11}$ is methyl.

7. The process of claim 1 wherein the compound of formula ASO$_2$Y is mesyl chloride or tosyl chloride.

8. The process of claim 1 wherein the agent to introduce K is mesyl chloride, tosyl chloride or 2,4,6-triisopropyl sulfonyl chloride.

9. The process of claim 1 wherein
   agent m is reacted with compound I in the presence of titanium tetrachloride and a tertiary aminated base or in the presence of an acid catalyst;

the protection of the amino is carried out by the action of phthalic anhydride on compound o or o';

the agent of formula HN=P is phthalic anhydride and the reaction with compound r is carried out in the presence of triphenylphosphine and an alkyl azobicarboxylate;

the rearrangement into tropolone is carried out by the action of acetic acid on compound u in the presence of an aminated base;

the deprotection of the amine is carried out by hydrazine;

the selective hydrolysis of compound x/x' is carried out with an alkaline thioalcoholate;

the reducing agent which is reacted on the oxime originating from compound v/v' is zinc in the presence of a sulfonic or carboxylic acid.

10. The process of claim 1 wherein the compound of formula v/v' wherein Z is

is subjected to the action of an agent capable of introducing the K group to obtain a compound of the formula

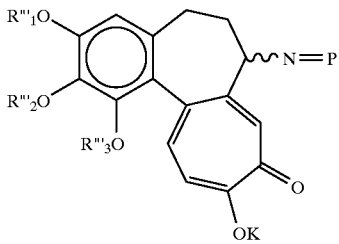

III which exists in a mixture with its regioisomer of formula:

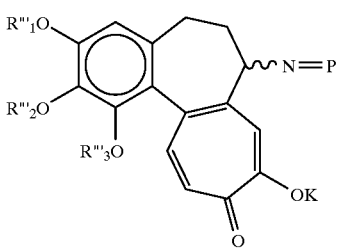

III' in which the wavy line indicates that the group is found in α- or β-position, or in a mixture of isomers and $R'''_1$, $R'''_2$, $R'''_3$, $R_{11}$ and K and alkyl have the meanings of claim 1, optionally separating the mixture, then the mixture or the separate constituents are subjected to a deprotection reaction of the amino to obtain either a compound of the formula

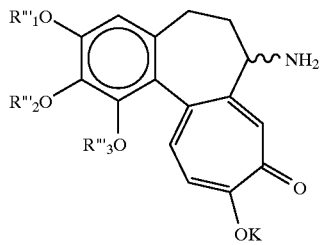

IV in the form of a mixture with its regioisomer of formula

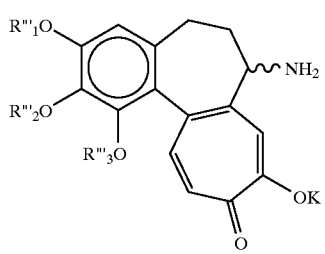

IV' which mixture, is optionally separated, or one or other of these regioisomers, then the mixture or the separate constituents are subjected to the action of a compound of the formula $R_{11}C(O)Y$ or $(R_{11}CO)_2O$, to obtain either the compound of formula II as defined above, in a mixture with its regioisomer of formula II', which mixture is optionally separated into its constituents, or one or other of these regioisomers.

11. The process of claim 10 wherein the agent capable of introducing K is selected from the group consisting of mesyl chloride, tosyl chloride and 2,4,6-triisopropyl sulfonyl chloride.

12. The process of claim 1 wherein a compound of the formula

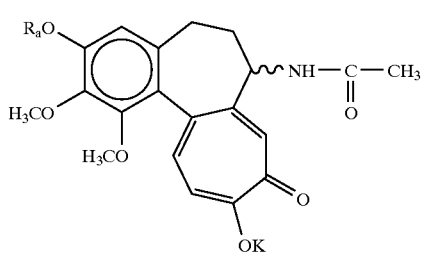

(II$_1$)

wherein Ra is $ASO_2$— and $ASO_2$—, K and the wavy line are as in claim 1, is reacted with $CH_3S^{31}$ Na+ to obtain a compound of the formula

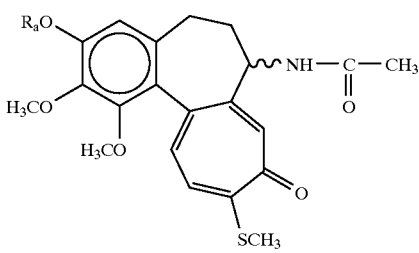

deprotecting the hydroxyl to obtain a compound of the formula

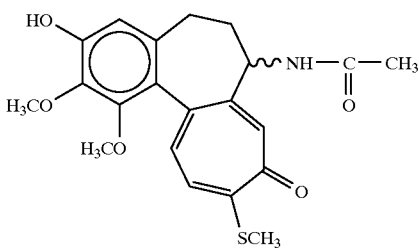

13. The process of claim 12 wherein the —OK substitution and the OH deprotection is effected with CH$_3$SNa.

14. The process of claim 1 wherein a compound of the formula

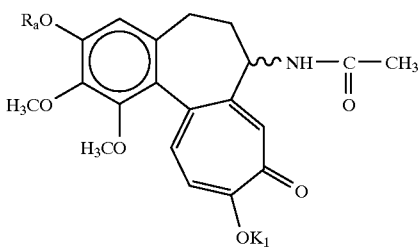

wherein K$_1$ is methyl and Ra and the wavy line are as in claim 1 is subjected to a deprotecting of the hydroxy to obtain a compound of the formula

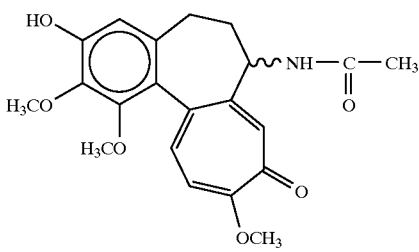

15. The process of claim 1 wherein a compound of the formula

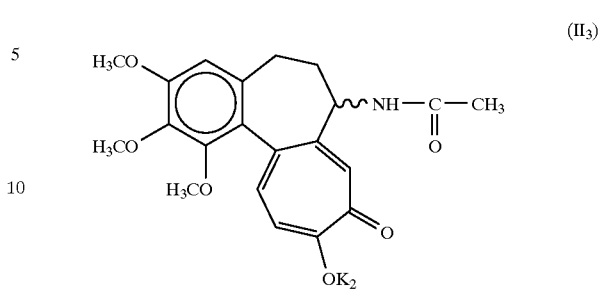

wherein K$_2$ is benzyl optionally substituted on the phenyl by 1 to 3 alkyls or A'SO$_2$— wherein A' and the wavy line are as in claim 1 is reacted with CH$_3$SNa to obtain a compound of the formula

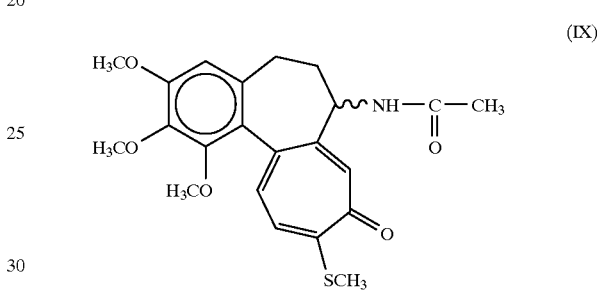

16. The process of claim 1 wherein a compound of the formula

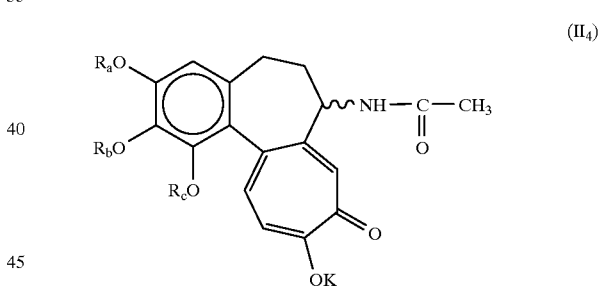

wherein R$_a$, K and the wavy line are as in claim 13 and R$_b$ and R$_c$ form —CR$_5$R$_6$— as defined in claim 13 is reacted with a deprotection agent of the diol to obtain a compound of the formula

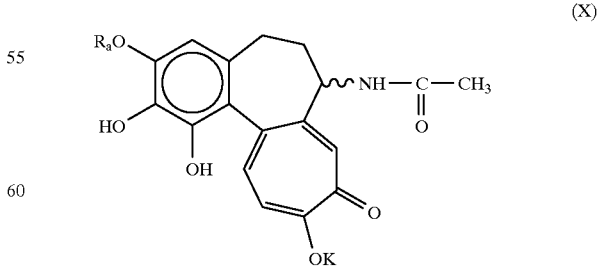

and reacting the latter with a methylation agent to form a compound of formula II as defined in claim 12 and the process of claim 12 is carried out.

17. A process of claim 1 wherein a compound of the formula

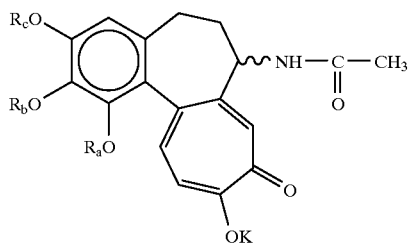
(II₅)

wherein $R_a$, K and the wavy line are as in claim 13 and $R_c$ and $R_b$ form —CR₅R₆— a defined in claim 13 is reacted with a deprotection agent of the diol to form a compound of the formula

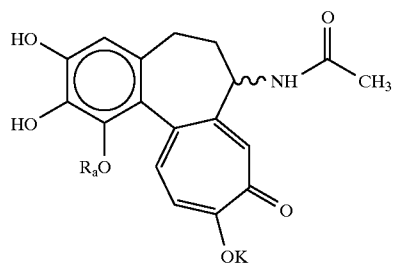
(XI)

wherein $R_a$, K and the wavy line are as above, reacting the latter with a hydrolysis agent to obtain a compound of the formula

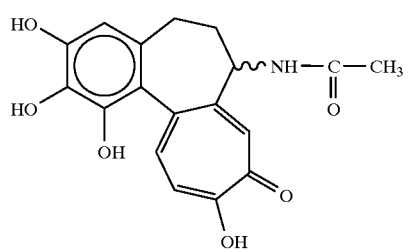
(XII)

and reacting the latter with a methylation agent to form colchicine.

* * * * *